(12) United States Patent
Communi et al.

(10) Patent No.: US 6,946,244 B2
(45) Date of Patent: Sep. 20, 2005

(54) METHODS OF IDENTIFYING A LIGAND, AN AGONIST, AND AN ANTAGONIST OF G PROTEIN COUPLED RECEPTOR GPR86 ($P2Y_{13}$)

(75) Inventors: Didier Communi, Dilbeek (BE); Nathalie Suarez, Brussels (BE); Michel Detheux, Mons (BE); Stephane Brezillion, Brussels (BE); Vincent Lannoy, Liernu (BE); Marc Parmentier, Linebeek (BE); Jean-Marie Boeynaems, Wammel (BE)

(73) Assignee: Euroscreen, S.A., Brussels (BE)

( * ) Notice: Subject to any disclaimer, the term of this patent is extended or adjusted under 35 U.S.C. 154(b) by 0 days.

(21) Appl. No.: 09/924,125

(22) Filed: Aug. 7, 2001

(65) Prior Publication Data

US 2003/0050235 A1 Mar. 13, 2003

(51) Int. Cl.[7] .............................. C12Q 1/00; C12Q 1/68; G01N 33/53; G01N 35/567
(52) U.S. Cl. .............................. 435/4; 435/7.1; 435/7.2; 435/7.21; 435/7.9; 435/6
(58) Field of Search .............................. 435/4, 7.1, 7.2, 435/7.21, 7.9, 6

(56) References Cited

U.S. PATENT DOCUMENTS 6,162,899 A   12/2000 Sathe et al. .................. 530/350

6,358,695 B1   3/2002 Sathe et al. .................. 435/7.2
2003/0059878 A1   3/2003 Onuki et al. ............... 435/69.1

FOREIGN PATENT DOCUMENTS

WO   WO-200053742 A2 * 9/2000

OTHER PUBLICATIONS

A-Geneseq, Accession No. AAB74397, Feb. 27, 2001.*
A-Geneseq, Accession No. AAB74494, 2001.*
Wittenberger, et al. *An Expressed Sequence Tag (EST) Data Mining Strategy Succeeding in the Discovery of New G–Protein Coupled Receptors.* (2001), J. Mol. Biol. 307:799–813.

* cited by examiner

Primary Examiner—Ruixiang Li
(74) Attorney, Agent, or Firm—Palmer & Dodge LLP; Kathleen M. Williams

(57) ABSTRACT

The present invention is related to a recombinant cell expressing a nucleotide sequence encoding a G protein coupled receptor having an amino acid sequence which presents more than 70% sequence identity with SEQ ID.NO.1 as well as to a drug screening method and kit using the orphan G protein coupled receptor GPR86, identified hereafter as receptor for ADP ($P2Y_{13}$) and a homologous sequence, the corresponding polynucleotide and said recombinant cell to identify agonist, inverse agonist and antagonist compounds applicable to a diagnostic, prevention and/or treatment of various diseases and disorders.

15 Claims, 13 Drawing Sheets

|       |       |       |
|-------|-------|-------|
| FIG. 1A |     |       |
| FIG. 1B |     |       |
| FIG. 1C |     |       |

FIG. 1

```
  1 ATG AAC ACC ACA GTG ATG CAA GGC TTC AAC AGA TCT GAG CGG TGC     45
  1  M   N   ■   T   V   M   Q   G   F   N   ■   S   E   R   C     15

46 CCC AGA GAC ACT CGG ATA GTA CAG CTG GTA TTC CCA GCC CTC TAC     90
 16  P   R   D   T   R   I   V   Q   L   V   F   P   A   L   Y     30

91 ACA GTG GTT TTC TTG ACC GGC ATC CCC AGC ACC TCC AAT ACT CTG    135
 31  T   V   V   F   L   T   G   I   P   S   T   S   N   T   L     45

136 TGG GTG TTT GTT CAC ATC CTT GTG GCC GAC TTG ATA ATG ACA CTC    180
 46  W   V   F   V   H   I   L   V   A   D   L   I   M   T   L     60

181 CTC AAA AAC ACT ATC CTC TCT GAC TCA CAC CTG GCA CCC TGG CAG    225
 61  L   K   N   T   I   L   S   D   S   H   L   A   P   W   Q     75

226 CCT TTC AAA ATC CTC CTT TCT GAC TTG ATA ATG ACA CTC ATG CTT    270
 76  P   F   K   I   L   L   S   D   L   I   M   T   L   M   L     90

271 AGA GCT TTT GTG TGT CGT TTT TCT TCG GTG ATA TTT TAT GAG ACC    315
 91  R   A   F   V   C   R   F   S   S   V   I   F   Y   E   T    105
```

FIG. 1A

```
316 ATG TAT GTG GGC ATC GTG CTG TTA GGG CTC ATA GCC TTT GAC AGA   360
106  M   Y   V   G   I   V   L   L   G   L   I   A   F   D   R   120
                         ───III───

361 TTC CTC AAG ATC ATC AGA CCT TTG AGA AAT ATT TTT CTA AAA AAA   405
121  F   L   K   I   I   R   P   L   R   N   I   F   L   K   K   135

406 CCT GTT TTT GCA AAA ACG TCA ATC GTC TTC ATC TGG TTC TTT TTG   450
136  P   V   F   A   K   T   V   S   I   F   I   W   F   F   L   150

451 TTC TTC ATC TCC CTG CCA AAT ATG ATC TTG AGC AAC AAG GAA GCA   495
151  F   F   I   S   L   P   N   M   I   L   S   N   K   E   A   165
                                         ───IV───

496 ACA CCA TCG TCT GTG AAA AAG TGT GCT TCC TTA AAG GGG CCT CTG   540
166  T   P   S   S   V   K   K   C   A   S   L   K   G   P   L   180

541 GGG CTG AAA TGG CAT CAA ATG GTA AAT AAC ATA TGC CAG TTT ATT   585
181  G   L   K   W   H   Q   M   V   N   N   I   C   Q   F   I   195

586 TTC TGG ACT GTT TTT ATC CTA ATG CTT GTG TTT TAT GTG GTT ATT   630
196  F   W   T   V   F   I   L   M   L   V   F   Y   V   V   I   210
                                     ───V───

631 GCA AAA AAA GTA TAT GAT TCT TAT AGA AAG TCC AAA AGT AAG GAC   675
211  A   K   K   V   Y   D   S   ●   Y   R   K   S   K   S   K   D   225

FIG. 1B
```

```
676  AGA AAA AAC AAC AAA AAG CTG GAA GGC AAA GTA TTT GTT GTC GTG   720
226   R   K   N   N   K   K   L   E   G   K   V   F   V   V   V   240
                                                  |_____VI_____
721  GCT GTC TTC TTT GTG TGT TTT GCT CCA TTT CAT TTT GCC AGA GTT   765
241   A   V   F   F   V   C   F   A   P   F   H   F   A   R   V   255
     _____|
766  CCA TAT ACT CAC AGT CAA ACC AAC AAT AAG ACT GAC TGT AGA CTG   810
256   P   Y   T   H   S   Q   T   N   N■  K   T   D   C   R   L   270
811  CAA AAT CAA CTG TTT ATT GCT AAA ACA ACT CTC TTT TTG GCA       855
271   Q   N   Q   L   F   I   A   K   T   T   L   F   L   A       285
856  GCA ACT AAC ATT TGT ATG GAT CCC TTA ATA TAC ATA TTC TTA TGT   900
286   A   T   N   I   C   M   D   P   L   I   Y   I   F   L   C   300
     ▲                        |_____VII____
901  AAA AAA TTC ACA GAA AAG CTA CCA TGT ATG CAA GGG AGA AAG ACC   945
301   K   K   F   T●  E   K   L   P   C   M   Q   G   R   K   T   315
946  ACA GCA TCA AGC CAA GAA AAT CAT AGC AGT CAG ACA GAC AAC ATA   990
316   T   A   S   S   Q   E   N   H   S   S   Q   T   D   N   I   330
991  ACC TTA GGC TGA                                               1002
331   T   L   G   *                                                334
```

FIG. 1C

METHODS OF IDENTIFYING A LIGAND, AN AGONIST, AND AN ANTAGONIST OF G PROTEIN COUPLED RECEPTOR GPR86 (P2Y$_{13}$)

FIELD OF THE INVENTION

The present invention is related to the natural ligand for the orphan G protein coupled receptor GPR86 and methods of use.

BACKGROUND OF THE INVENTION AND STATE OF THE ART

Adenine and uridine nucleotides induce pharmacological and physiological responses through several G-protein-coupled receptors (P2Y) and ligand-gated cation channels (P2X) (1, 2). The P2Y family encompasses two selective purinoceptors: the human P2Y$_1$ and P2Y$_{11}$ receptors which are preferentially activated respectively by ADP and ATP (3–5). Nucleotide receptors responsive to both adenine and uracil nucleotides are the P2Y$_2$ receptor, activated equipotently by ATP and UTP (6, 7) as well as the Xenopus P2Y$_8$ (8) and turkey tp2y receptor (9) activated equally by all triphosphate nucleotides. There are also pyrimidinoceptors: the chicken P2Y$_3$ (10) and human P2Y$_6$ (11–13) receptors activated preferentially by UDP, and the human P2Y$_4$ receptor (13–15) activated preferentially by UTP. All these P2Y subtypes are coupled to the phosphoinositide pathway. The P2Y$_{11}$ and tp2y receptors are additionally coupled respectively to stimulation and inhibition of adenylyl cyclase. Other receptors (P2Y$_5$ (16), P2Y$_7$ (17), P2Y$_9$ and P2Y$_{10}$) have been mistakenly included in the P2Y family (18–20). Recently, a P2Y$_{12}$ subtype has been cloned which corresponds to the platelet ADP receptor previously called P$_{2T}$ (21, 22). It is coupled to an inhibition of adenylyl cyclase and is specifically expressed in the platelets and the brain. Its primary structure is not related to the other P2Y receptors but is related to that of the UDP-glucose receptor (23).

More than 300 G protein coupled receptors (GPCRs) have been cloned thus far and it is generally assumed that well over 1000 such receptors exist. Mechanistically, approximately 30–50% of all clinically relevant drugs act by modulating the functions of various GPCRs (34).

Known and unknown GPCRs now constitute major targets for drug action and development.

GPR86 is a member of the rhodopsin-like receptor family, cloned in 1997 (24). It shows a homology of 49% with the recently identified platelet ADP receptor, P2T.

The identified ORF of 1002 bp of said receptor is preceded by a stop codon 18 bp upstream, and the putative poly(A) signal AATAAA is present 1672 bp downstream of the coding sequence. hGPR86 has the same genomic localization as hGPR87 on chromosome 3q24, but in contrast to hGPR87, its coding sequence is intronless. The deduced 333 amino acid residue sequence of hGPR86 shows the typical 7 transmembrane (7TM) structure of a GPCR, with no signal peptide. It exhibits essentially the same motifs as described for GPR87 and KIAA0001, and therefore is also a member of family 1 GPCRs. Instead of the DRY motif there is a DRF motif present which is also seen in the sequences of purinergic receptors, the C5A and Bonzo receptors, and the thrombin receptor precursors.

SUMMARY OF THE INVENTION

The present invention is related to the GPR86 (P2Y$_{13}$) receptor (or any homologous sequence), the nucleic acid sequence of which is set forth in SEQ ID NO: 1 and the amino acid sequence of which is set forth in SEQ ID NO: 2 and a recombinant cell (transformed by a suitable vector) comprising the nucleotide sequence encoding the receptor, as well as the natural ligands (ADP and equivalent molecules such as 2MeSADP, ADPβS including any of the ADP analogues presented in U.S. Pat. NO. 5,700,786) to be used in screening assays for identification of agonists, inverse agonists or antagonist compounds useful for the development of new drugs and the improvement of various disease diagnostics.

A homologous sequence (which may exist in other mammal species or specific groups of human populations), where homology indicates sequence identity, means a sequence which presents a high sequence identity (more than 70%, 75%, 80%, 85%, 90%, 95% or 98% sequence identity) with the complete human nucleotide or amino acid sequence described hereafter, and is preferably characterized by the same pharmacology, especially a preference for binding to ADP>>IDP>UDP (the affinity of ADP for GPR86 was approximately 1000-fold greater than that of IDP and UDP (ADP>IDP>UDP)).

Preferably, the recombinant cell according to the invention is a recombinant cell transformed by a plasmid or viral vector, preferably a baculovirus, an adenovirus, a semliki forest virus, and the cell is preferably selected from the group consisting of bacterial cells, yeast cells, insect cells or mammal cells.

According to a preferred embodiment of the present invention, the cell is selected from the group consisting of COS-7 cells, a CHO cell, a LM (TK−) cell, a NIH-3T3 cell, HEK-293 cell, K-562 cell or a 1321N1 astrocytoma cell but also other transfectable cell lines. Preferably, the vector comprises all the regulatory elements, operatively linked to the polynucleotide sequence encoding the receptor according to the invention so as to permit expression thereof.

Another aspect of the present invention is related to the use of a specific active portion of the sequences. As used herein, an "active portion" refers to a portion of a sequence that is of sufficient size to exhibit normal or near normal pharmacology (e.g., receptor activity (as defined herein), the response to an activator or inhibitor, or ligand binding are at least 90% of the level of activity, response, or binding exhibited by a wild type receptor). "A portion" as it refers to a sequence encoding a receptor, refers to less than 100% of the sequence (i.e., 99, 90, 80, 70, 60, 50% etc . . . ). The active portion could be a receptor which comprises a partial deletion of the complete nucleotide or amino acid sequence and which still maintains the active site(s) and protein domain(s) necessary for the binding of and interaction with a specific ligand, preferably ADP.

In another embodiment of any of the preceding methods, the contacting is performed in or on synthetic liposomes (see Tajib Mirzabekov, Harry Kontos, Michael Farzan, Wayne Marasco, Joseph Sodroski (2000) Paramagnetic proteoliposomes containing a pure, native, and oriented seven-transmembrane segment protein, CCR5. Nature Biotechnology 18, 649–654, which is incorporated herein by reference) or virus-induced budding membranes containing a GPR86 polypeptide. (See Patent application WO0102551, Virus-like particles, their Preparation and their Use preferably in Pharmaceutical Screening and Functional Genomics (2001) incorporated herein by references.)

As used herein, "ligand" refers to a moiety that is capable of associating or binding to a receptor. According to the method of the invention, a ligand and a receptor have a binding constant that is sufficiently strong to allow detection of binding by an assay method that is appropriate for detection of a ligand binding to a receptor (e.g. a second messenger assay to detect an increase or decrease in the production of a second messenger in response to ligand binding to the receptor, a binding assay to measure protein-ligand binding or an immunoassay to measure antibody-antigen interactions). A ligand according to the invention includes the actual molecule that binds a receptor (e.g. ADP is the ligand for GPR86) or a ligand may be any nucleotide, antibody, antigen, enzyme, peptide, polypeptide or nucleic acid capable of binding to the receptor. A ligand is preferably a nucleotide but can also include a polypeptide, a peptide or a nucleic acid sequence. According to the method of the invention, a ligand and receptor specifically bind to each other (e.g. via covalent or hydrogen bonding or via an interaction between, for example, a protein and a ligand, an antibody and an antigen or protein subunits).

As used herein, "ADP" refers to a nucleotide that is produced by hydrolysis of the terminal phosphate of ATP and has a structure comprising adenine, ribose and two phosphate groups (FIG. 7). It is contemplated that analogs of ADP will be considered as ADP equivalents. ADP analogs according to the invention include 2MeSADP, ADPβS. An ADP analog according to the invention will exhibit the same basic structure as ADP, defined above and presented in FIG. 7, as well as one or more different substituent groups including but not limited to any of the ADP analogues presented in U.S. Pat. No. 5,700,786. An ADP analog according to the invention will exhibit binding to GPR86 that is equivalent to ADP.

As used herein, "GPR activity" refers to the activity of a receptor comprising the sequence presented in FIG. 1, or a sequence that exhibits at least 70% identity (for example, 70%, 75%, 80%, 90%, 95% etc . . . ) with the sequence presented in FIG. 1. A receptor that has "GPR activity" will bind to ADP with an affinity that is at least 100-fold, preferably 500-fold and most preferably 1000-fold greater than that of IDP and UDP (ADP>IDP>UDP).

Homologous sequences of a sequence according to the invention may include an amino acid or nucleotide sequence encoding a similar receptor which exists in other animal species (rat, mouse, cat, dog, etc.) or in specific human population groups, but which are involved in the same biochemical pathway.

Such homologous sequences may comprise additions, deletions or substitutions of one or more amino acids or nucleotides, which do not substantially alter the functional characteristics of the receptor according to the invention.

Such homologous sequences can also be nucleotide sequences of more than 400, 600, 800 or 1000 nucleotides able to hybridize to the complete human sequence under stringent hybridisation conditions (such as the ones described by SAMBROOK et al., Molecular Cloning, Laboratory Manuel, Cold Spring, Harbor Laboratory press, New York).

Another aspect of the present invention is related to a method for the screening, detection and possible recovery of candidate modulators of a receptor of the invention comprising the steps of: contacting a cell expressing GPR86 under conditions which permit binding of ADP to GPR86, in the presence of the candidate modulator, performing a second messenger assay, and comparing the results of the second messenger assay obtained in the presence and absence of the candidate modulator.

Another aspect of the present invention is related to a method for the screening, detection and possible recovery of candidate modulators of a receptor of the invention comprising the steps of: contacting a cell membrane expressing GPR86 under conditions which permit binding of ADP to GPR86 performing a second messenger assay, and comparing the results of the second messenger assay obtained in the presence and absence of the candidate modulator.

In another embodiment, a candidate modulator or compound is selected from the group consisting of a natural or synthetic peptide, a polypeptide, an antibody or antigen-binding fragment thereof, a lipid, a carbohydrate, a nucleic acid, and a small organic molecule.

In another embodiment, the step of measuring a signalling activity of the GPR86 polypeptide comprises detecting a change in the level of a second messenger.

A further aspect of the present invention is related to the unknown agonist and/or antagonist compounds identified and/or recovered by the method of the invention, as well as to a diagnostic kit comprising said (unknown) compounds or a pharmaceutical composition (including a vaccine) comprising an adequate pharmaceutical carrier and a sufficient amount of said (unknown) compound.

An antagonist compound according to the invention means a molecule or a group of molecules able to bind to the receptor according to the invention and block the binding of natural compounds (ADP or an equivalent molecule, for example 2MeSADP or ADPβS including but not limited to any of the ADP analogues presented in U.S. Pat. No. 5,700,786).

The invention further encompasses a method of detecting the presence, in a sample, of an agent that modulates the function of GPR86, the method comprising: a) contacting a GPR86 polypeptide with the sample; b) detecting a signalling activity of the GPR86 polypeptide in the presence of the sample; and c) comparing the activity measured in the presence of the sample to the activity measured in a reaction with GPR86 polypeptide and ADP at EC50, wherein an agent that modulates the function of GPR86 is detected if the amount of the GPR86-specific activity measured in the presence of the sample is at least 10% that of the amount induced by ADP present at its EC50.

The invention further encompasses a method of diagnosing a disease or disorder characterized by dysregulation of GPR86 signalling, the method comprising: a) contacting a tissue sample with an antibody specific for a GPR86 polypeptide; b) detecting binding of the antibody to the tissue sample; and c) comparing the binding detected in step (b) with a standard, wherein a difference in binding relative to the standard is diagnostic of a disease or disorder characterized by dysregulation of GPR86.

The invention further encompasses a method of diagnosing a disease or disorder characterized by dysregulation of GPR86 signalling, the method comprising: a) contacting a tissue sample with an antibody specific for a GPR86 ligand; b) detecting binding of the antibody to the tissue sample; and c) comparing the binding detected in step (b) with a standard, wherein a difference in binding relative to the standard is diagnostic of a disease or disorder characterized by dysregulation of GPR86.

The invention further encompasses a method of diagnosing a disease or disorder characterized by dysregulation of GPR86 signalling, the method comprising: a) contacting a tissue sample with an antibody specific for a GPR86 polypeptide and an antibody specific for a GPR86 ligand; b) detecting binding of the antibodies to the tissue sample; and c) comparing the binding detected in step (b) with a standard, wherein a difference in binding of either antibody or both, relative to the standard, is diagnostic of a disease or disorder characterized by dysregulation of GPR86.

The invention further encompasses a method of diagnosing a disease or disorder characterized by dysregulation of GPR86 signalling, the method comprising: a) isolating nucleic acid from a tissue sample; b) amplifying a GPR86 polynucleotide, using the nucleic acid as a template; and c) comparing the amount of amplified GPR86 polynucleotide produced in step (b) with a standard, wherein a difference in the amount of amplified GPR86 polynucleotide relative to the standard is diagnostic of a disease or disorder characterized by dysregulation of GPR86.

In a preferred embodiment, the step of amplifying comprises RT/PCR. In another preferred embodiment, the standard is SEQ ID NO: 1. In another preferred embodiment, the step of comparing the sequence comprises minisequencing. In another preferred embodiment, the step of comparing the amount is performed on a microarray.

The invention further encompasses a method of diagnosing a disease or disorder characterized by dysregulation of GPR86 signalling, the method comprising: a) isolating nucleic acid from a tissue sample; b) amplifying a polynucleotide that encodes a GPR86-specific polypeptide ligand, using the nucleic acid as a template; and c) comparing the amount of amplified GPR86-specific ligand polynucleotide produced in step (b) with a standard, wherein a difference in the amount of amplified GPR86-specific ligand polynucleotide relative to the standard is diagnostic of a disease or disorder characterized by dysregulation of GPR86.

In a preferred embodiment, the step of amplifying comprises RT/PCR. In another preferred embodiment, the step of comparing the sequence comprises minisequencing. In another preferred embodiment, the step of comparing the sequence is performed on a microarray.

A further aspect of the present invention is related to a transgenic non-human mammal, comprising a homologous recombination (knock-out) of the polynucleotide encoding the GPR86 ($P2Y_{13}$) receptor according to the invention or a transgenic non-human mammal over expressing the polypeptide above the natural level of expression. As used herein, "above the natural level of expression" refers to a level that is at least 2-fold, preferably 5-fold, more preferably 10-fold and most preferably 100-fold or more (i.e., 150-fold, 200-fold, 250-fold, 500-fold, 1000-fold, 10,000-fold etc.) as compared to the level of expression of the endogenous receptor. A transgenic non-human mammal can be obtained by a method well known by a person skilled in the art, for instance, as described in document WO 98/20112 using the classical technique based upon the transfection of embryonic stem cells, preferably according to the method described by Carmeliet et al. (Nature, Vol.380, p.435–439, 1996).

"Gene targeting" is a type of homologous recombination that occurs when a fragment of genomic DNA is introduced into a mammalian cell and that fragment locates and recombines with endogenous homologous sequences as exemplified in U.S. Pat. Nos. 5,464,764, and 5,777,195, the contents of which are hereby incorporated by reference herein in their entireties. As used herein the term "transgenic animal" refers to a non-human animal in which one or more, and preferably essentially all, of the cells of the animal contain a transgene introduced by way of human intervention, such as by transgenic techniques known in the art. The transgene can be introduced into the cell, directly or indirectly by introduction into a precursor of the cell, by way of deliberate genetic manipulation, such as by microinjection or by infection with a recombinant virus.

Preferably, the transgenic non-human mammal overexpressing the polynucleotide encoding the GPR86 ($P2Y_{13}$) receptor according to the invention comprises the polynucleotide incorporated in a DNA construct with an inducible promoter allowing the overexpression of the receptor and possibly also tissue and cell-specific regulatory elements.

The diagnostic kit according to the invention includes at least GPR86 receptor and, packaged separately, ADP and also may comprise advantageously all the necessary means and media for performing a detection of specific binding (for example of ADP) to the GPR86 receptor of the invention and possibly correlating the detection of specific binding to a method of monitoring of one or more of the symptoms of the diseases described hereafter.

Possibly, the kit comprises elements for a specific diagnostic or dosage of such bound compounds through high throughput screening techniques, well known to the person skilled in the art, especially the one described in WO 00/02045. The high throughput screening diagnostic dosage and monitoring can be performed by using various solid supports, such as microtiter plates or biochips selected by the person skilled in the art.

In the pharmaceutical composition according to the invention, the adequate pharmaceutical carrier is a carrier of solid liquid or gaseous form, which can be selected by the person skilled in the art according to the type of administration and the possible side effects of the compound according to the invention. The ratio between the pharmaceutical carrier and the specific compound can be selected by the person skilled in the art according to the patient treated, the administration and the possible side effects of the compound, as well as the type of disease of disorder treated or submitted to a specific prevention.

1. The pharmaceutical composition finds advantageous applications in the field of treatment and/or prevention of various diseases or disorders, preferably selected from the group consisting of ostatic hypertrophy, migraine, vomiting, psychotic and neurological disorders, including anxiety, schizophrenia, maniac depression, depression, delirium, dementia and severe mental retardation, degenerative diseases, neurodegenerative diseases such as Alzheimer's disease or Parkinson's disease, and dyskinasias, such as Huntington's disease or Gilles de la Tourett's syndrome and other related diseases including thrombosis and other cardiovascular diseases, autoimmune and inflammatory diseases.

2. Among the mentioned diseases the preferred applications are related to therapeutic agents targeting 7TM receptors that can play a function in preventing, improving or correcting dysfunctions or diseases, including, but not limited to fertility, fetal development, infections such as bacterial, fungal, protozoan and viral infections, particularly infections caused by HIV1 and HIV2, pain, cancer, anorexia, bulimia, asthma, Parkinson's disease, acute heart failure, hypertension, urinary retention, osteoporosis, angina pectoris, myocardial infarction, ulcers, asthma, allergies, benign prostatic hypertrophy, psychotic and neurological disorders including anxiety, depression, migraine, vomiting, stroke, schizophrenia, manic depression, delirium, dementia, severe mental retardation and dyskinesias, such as Huntington's disease or Gilles de la Tourette's syndrome including thrombosis and other cardiovascular diseases, autoimmune and inflammatory diseases.

As used herein, an "antagonist" is a ligand which competitively binds to the receptor at the same site as an agonist, but does not activate an intracellular response initiated by an active form of a receptor, and thereby inhibits the intracellular response induced by an agonist, for example ADP, by at least 10%, preferably 15–25%, more preferably 25–50% and most preferably, 50–100%, as compared to the intracellular response in the presence of an agonist and in the absence of an antagonist.

As used herein, an "agonist" refers to a ligand, that activates an intracellular response when it binds to a receptor at concentrations equal or lower to ADP concentrations which induce an intracellular response. An agonist according to the invention may increase the intracellular response mediated by a receptor by at least 2-fold, preferably 5-fold, more preferably 10-fold and most preferably 100-fold or more (i.e., 150-fold, 200-fold, 250-fold, 500-fold, 1000-fold, 10,000-fold etc . . . ), as compared to the intracellular response in the absence of agonist. An agonist, according to the invention may decrease internalization of a cell surface receptor such that the cell surface expression of a receptor is increased by at least 2-fold, preferably 5-fold, more preferably 10-fold and most preferably, 100-fold or more (i.e., 150-fold, 200-fold, 250-fold, 500-fold, 1000-fold, 10,000-fold etc . . . ), as compared to the number of cell surface receptors present on the surface of a cell in the absence of an agonist. In another embodiment of the invention, an agonist stablizes a cell surface receptor and increases the cell surface expression of a receptor by at least 2-fold, preferably 5-fold, more preferably 10-fold and most preferably, 100-fold or more (i.e., 200-fold, 250-fold, 500-fold, 1000-fold, 10,000-fold etc . . . ), as compared to the number of cell surface receptors present on the surface of a cell in the absence of agonist.

As used herein, an "inverse agonist" refers to a ligand which decreases a constitutive activity of a cell surface receptor when it binds to a receptor. An inverse agonist according to the invention may decrease the constitutive intracellular response mediated by a receptor by at least 2-fold, preferably 5-fold, more preferably 10-fold and most preferably 100-fold or more (i.e., 150-fold, 200-fold, 250-fold, 500-fold, 1000-fold, 10,000-fold etc . . . ), as compared to the intracellular response in the absence of inverse agonist.

An "inhibitor" compound according to the invention is a molecule directed against the receptor or against the natural ligand for the receptor that decreases the binding of the ligand to the receptor by at least 10%, preferably 15–25%, more preferably 25–50% and most preferably, 50–100%, in the presence of ADP, as compared to the binding in the presence of ADP and in the absence of inhibitor. An "inhibitor" compound of the invention can decrease the intracellular response induced by an agonist, for example ADP, by at least 10%, preferably 15–25%, more preferably 25–50% and most preferably, 50–100%. An "inhibitor" also refers to a nucleotide sequence encoding an inhibitor compound of the invention.

As used herein, "natural ligand" refers to a naturally occurring ligand, found in nature, which binds to a receptor in a manner that is equivalent to ADP (i.e., with an affinity for the ligand that is greater than the affinity of IDP and UDP (ADP>IDP>UDP). A "natural ligand" does not refer to an engineered ligand that is not found in nature and that is engineered to bind to a receptor, where it did not formerly do so in a manner different, either in degree or kind from that which it was engineered to do, it is no longer naturally-occurring but is "non-natural" and is derived from a naturally occurring molecule.

As used herein, a "modulator" refers to any compound that increases or decreases the cell surface expression of a receptor of the invention, increases or decreases the binding of a ligand to a receptor of the invention, or any compound that increases or decreases the intracellular response initiated by an active form of the receptor of the invention, either in the presence or absence or an agonist, and in the presence of a ligand for the receptor, for example ADP. A modulator includes an agonist, antagonist, inhibitor or inverse agonist, as defined herein. A modulator can be a protein, a nucleic acid, an antibody or fragment thereof, a peptide, etc . . . Candidate modulators can be natural or synthetic compounds, including, for example, small molecules, compounds contained in extracts of animal, plant, bacterial or fungal cells, as well as conditioned medium from such cells.

As used herein, the term "small molecule" refers to a compound having molecular mass of less than 3000 Daltons, preferably less than 2000 or 1500, still more preferably less than 1000, and most preferably less than 600 Daltons. A "small organic molecule" is a small molecule that comprises carbon.

As used herein, the term "change in binding" or "change in activity" and the equivalent terms "difference in binding" or "difference in activity" or difference in the amount of "amplified" PCR product refer to an at least 10% increase or decrease in binding relative to the standard, or signalling activity or mRNA levels relative to the standard in a given assay.

As used herein, the term "dysregulation" refers to the signalling activity of GPR86 in a sample wherein:

a) a 10% increase or decrease in the amount of GPR86 or GPR86 polypeptide ligand mRNA or polypeptide levels is measured relative to the standard, as defined herein, of a given assay, or;

b) at least a single base pair change in the GPR86 or GPR86 polypeptide ligand coding sequence is detected relative to the standard, as defined herein, of a given assay and results in an alteration of GPR signalling activity as defined in paragraphs a), c), or d), or;

c) a 10% increase or decrease in the amount of GPR86 ligand binding activity is measured relative to the standard, as defined herein, of a given assay, or;

d) a 10% increase or decrease in secondary messenger assays, as defined herein, is measured relative to the standard, as defined herein, of a given assay.

As used herein, the term "conditions permitting the binding of ADP to GPR86" refers to conditions of, for example, temperature, salt concentration, pH and protein concentration under which ADP binds GPR86. Exact binding conditions will vary depending upon the nature of the assay, for example, whether the assay uses viable cells or only membrane fraction of cells. However, because GPR86 is a cell surface protein favored conditions will generally include physiological salt (90 mM) and pH (about 7.0 to 8.0). Temperatures for binding can vary from 15° C. to 37° C., but will preferably be between room temperature and about 30° C. The concentration of ADP and GPR86 polypeptide in a binding reaction will also vary, but will preferably be about 0.1 nM (e.g., in a reaction with radiolabelled tracer ADP, where the concentration is generally below the $K_d$) to 1 $\mu$M (e.g., ADP as competitor).

As used herein, the term "sample" refers to the source of molecules being tested for the presence of an agent or modulator compound that modulates binding to or signalling activity of a GPR86 polypeptide. A sample can be an environmental sample, a natural extract of animal, plant yeast or bacterial cells or tissues, a clinical sample, a synthetic sample, or a conditioned medium from recombinant cells or a fermentation process. The term "tissue sample" refers to a tissue that is tested for the presence, abundance, quality or an activity of a GPR86 polypeptide, a nucleic acid encoding a GPR86 polypeptide, or an agent or compound that modifies the ligand binding or activity of a GPR86 polypeptide.

As used herein, a "tissue" is an aggregate of cells that perform a particular function in an organism. The term "tissue" as used herein refers to cellular material from a particular physiological region. The cells in a particular tissue can comprise several different cell types. A non-limiting example of this would be brain tissue that further comprises neurons and glial cells, as well as capillary endothelial cells and blood cells, all contained in a given tissue section or sample. In addition to solid tissues, the term "tissue" is also intended to encompass non-solid tissues, such as blood.

As used herein, the term "membrane fraction" refers to a preparation of cellular lipid membranes comprising a GPR86 polypeptide. As the term is used herein, a "membrane fraction" is distinct from a cellular homogenate, in that at least a portion (i.e., at least 10%, and preferably more) of non-membrane-associated cellular constituents has been removed. The term "membrane associated" refers to those cellular constituents that are either integrated into a lipid membrane or are physically associated with a component that is integrated into a lipid membrane.

As used herein, the "second messenger assay" preferably comprises the measurement of guanine nucleotide binding or exchange, adenylate cyclase, intra-cellular cAMP, intra-cellular inositol phosphate, intra-cellular diacylglycerol concentration, arachinoid acid concentration, MAP kinase(s) or tyrosine kinase(s), protein kinase C activity, or reporter gene expression or an aequorin-based assay according to methods known in the art and defined herein.

As used herein, the term "second messenger" refers to a molecule, generated or caused to vary in concentration by the activation of a G-Protein Coupled Receptor, that participates in the transduction of a signal from that GPCR. Non-limiting examples of second messengers include cAMP, diacylglyceorl, inositol triphosphate, arachidonic acid release, inositol triphosphates and intracellular calcium. The term "change in the level of a second messenger" refers to an increase or decrease of at least 10% in the detected level of a given second messenger relative to the amount detected in an assay performed in the absence of a candidate modulator.

As used herein, the term "aequorin-based assay" refers to an assay for GPCR activity that measures intracellular calcium flux induced by activated GPCRs, wherein intracellular calcium flux is measured by the luminescence of aequorin expressed in the cell.

As used herein, the term "binding" refers to the physical association of a ligand (e.g., ADP or an antibody) with a receptor (e.g., GPR86). As the term is used herein, binding is "specific" if it occurs with an $EC_{50}$ or a $K_d$ of 100 nM or less, generally in the range of 100 nM to 10 pM. For example, binding is specific if the $EC_{50}$ or $K_d$ is 100 nM, 50 nM, 10 nM, 1 nM, 950 pM, 900 pM, 850 pM, 800 pM, 750 pM, 700 pM, 650 pM, 600 pM, 550 pM, 500 pM, 450 pM, 400 pM, 350 pM, 300 pM, 250 pM, 200 pM, 150 pM, 100 pM, 75 pM, 50 pM, 25 pM or 10 pM or less.

As used herein, the term "$EC_{50}$," refers to that concentration of a compound at which a given activity, including binding of ADP or other ligand and a functional activity of a GPR86 polypeptide, is 50% of the maximum for that GPR86 activity measurable using the same assay in the absence of compound. Stated differently, the "$EC_{50}$" is the concentration of compound that gives 50% activation, when 100% activation is set at the amount of activity that does not increase with the addition of more agonist. It should be noted that the "$EC_{50}$ of ADP" will vary according to the identity of the ADP analogue used in the assay; for example, ADP analogues can have $EC_{50}$ values higher than, lower than or the same as ADP. Therefore, where an ADP analogue differs from ADP, one of the skill in the art can determine the $EC_{50}$ for that analogue according to conventional methods. The $EC_{50}$ of a given ADP is measured by performing an assay for the activity of a fixed amount of GPR86 polypeptide in the presence of doses of ADP that increase at least until the GPR86 response is saturated or maximal, and then plotting the measured GPR86 activity versus the concentration of ADP.

As used herein, the term "saturation" refers to the concentration of ADP or other ligand at which further increases in ligand concentration fail to increase the binding of ADP ligand or GRP86-specific signalling activity.

As used herein, the term "$IC_{50}$" is the concentration of an antagonist or inverse agonist that reduces the maximal activation of a GPR86 receptor by 50%.

As used herein, the term "decrease in binding" refers to a decrease of at least 10% in the amount of binding detected in a given assay with a known or suspected modulator of GPR86 relative to binding detected in an assay lacking that known or suspected modulator.

As used herein, the term "delivering," when used in reference to a drug or agent, means the addition of the drug or agent to an assay mixture, or to a cell in culture. The term also refers to the administration of the drug or agent to an animal. Such administration can be, for example, by injection (in a suitable carrier, e.g., sterile saline or water) or by inhalation, or by an oral, transdermal, rectal, vaginal, or other common route of drug administration.

As used herein, the term "standard" refers to a sample taken from an individual who is not affected by a disease or disorder characterized by dysregulation of GPR86 activity. The "standard" is used as a reference for the comparison of GPR86 mRNA levels and quality (i.e., mutant vs wild type), as well as for the comparison of GPR86 activities.

As used herein, the term "amplifying," when applied to a nucleic acid sequence, refers to a proccess whereby one or more copies of a nucleic acid sequence is generated from a template nucleic acid. A preferred method of "amplifying" is PCR or RT/PCR.

As used herein, the term "G-Protein coupled receptor," or "GPCR" refers to a membrane-associated polypeptide with 7 alpha helical transmembrane domains. Functional GPCR's associate with a ligand or agonist and also associate with and activate G-proteins. GPR86 is a GPCR.

As used herein, the term "antibody" is the conventional immunoglobulin molecule, as well as fragments thereof which are also specifically reactive with one of the subject polypeptides. Antibodies can be fragmented using conventional techniques and the fragments screened for utility in the same manner as described herein below for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanised molecules having affinity for a polypeptide conferred by at least one CDR region of the antibody. In preferred embodiments, the antibody further comprises a label attached thereto and able to be detected, (e.g., the label can be a radioisotope, fluorescent compound, chemiluminescent compound, enzyme, or enzyme co-factor). The antibodies, monoclonal or polyclonal and its hypervariable portion thereof (FAB, FAB", etc.) as well as the hybridoma cell producing the antibodies are a further aspect of the present invention which find a specific industrial application in the field of diagnostics and monitoring of specific diseases, preferably the ones hereafter described.

Inhibitors according to the invention include but are not limited to labeled monoclonal or polyclonal antibodies or hypervariable portions of the antibodies.

As used herein, the term "transgenic animal" refers to any animal, preferably a non-human mammal, bird, fish or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule This molecule may be integrated within a chromosome, or it may be extra-chromosomally replicating DNA. In the typical transgenic animals described herein, the transgene causes cells to express a recombinant form of one of the subject polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

BRIEF DESCRIPTION OF FIGURES

FIGS. 1A to 1C represent nucleotide (SEQ ID NO: 1) and deduced amino acid sequence (SEQ ID NO: 2) of the human GPR86 ($P2Y_{13}$) receptor according to the invention.

DETAILED DESCRIPTION OF THE INVENTION

Figure 2:
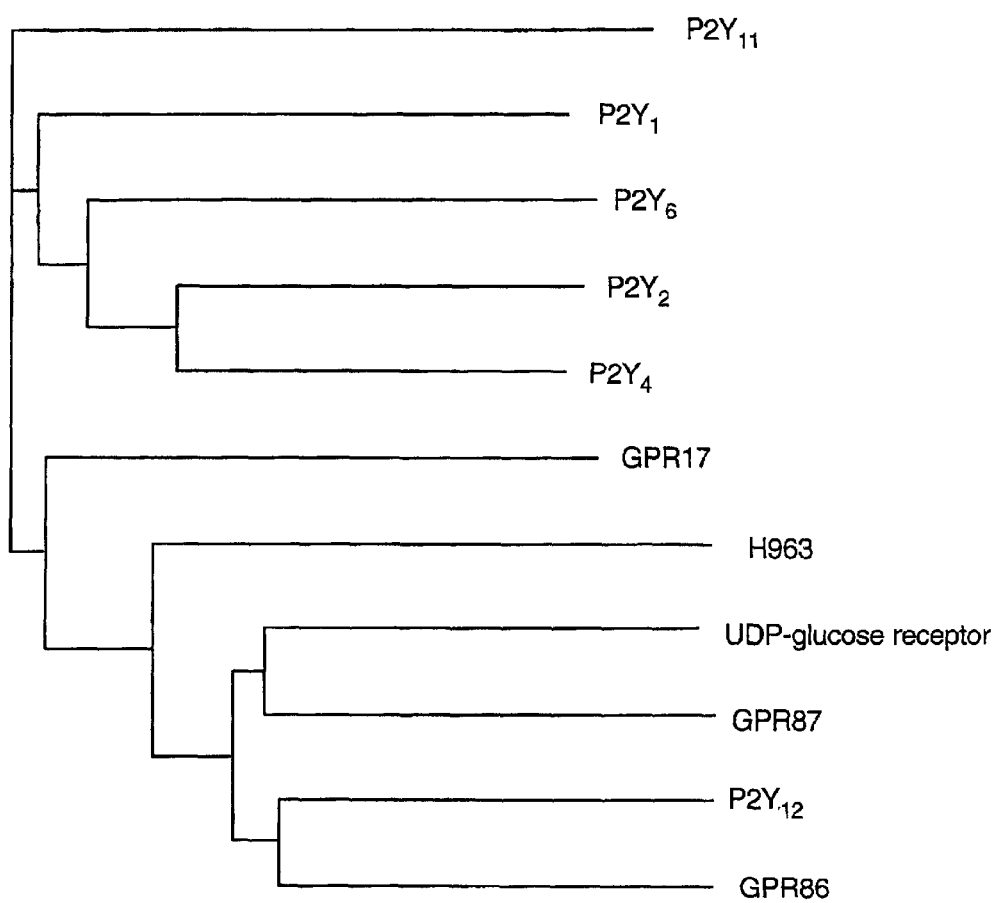
FIG. 2 is a dendrogram representing the structural relatedness of the GPR86 ($P2Y_{13}$) receptor with the other P2Y subtypes.

The invention relates to the discovery that ADP is a natural ligand for the orphan G protein coupled receptor GPR86 and methods of using the binding of this ligand to the receptor in a drug screening method. The known ligand and its interaction with the receptor GPR86 also provides for the diagnosis of conditions involving dysregulated receptor activity. The invention also relates to a kit comprising GPR86 ($P2Y_{13}$) and homologous sequences, its corresponding polynucleotide and/or recombinant cells expressing the polynucleotide, to identify agonist, antagonist and inverse agonists compounds of the receptor polypeptide and/or its corresponding polynucleotide. Such kits are useful for the diagnosis, prevention and/or a treatment of various diseases and disorders.

The invention also relates to novel agonist, antagonist and inverse agonists compounds of the receptor polypeptide and its corresponding polynucleotide, identified according to the method of the invention.

All references referred to below and above are incorporated by reference in their entirety.

Sequences

The invention relates to the nucleotide and amino acid sequences encoding GPR86 (presented in FIG. 1). The invention also relates to sequences that are homologous to the nucleotide and amino acid sequences encoding GPR86.

Calculation of Sequence Homology

Sequence identity with respect to any of the sequences presented herein can be determined by a simple "eyeball" comparison (i.e. a strict comparison) of any one or more of the sequences with another sequence to see if that other sequence has, for example, at least 70% sequence identity to the sequence(s).

Relative sequence identity can also be determined by commercially available computer programs that can calculate % identity between two or more sequences using any suitable algorithm for determining identity, using for example default parameters. A typical example of such a computer program is CLUSTAL. Other computer program methods to determine identity and similarity between two sequences include but are not limited to the GCG program package (Devereux et al 1984 Nucleic Acids Research 12: 387) and FASTA (Atschul,l et al 1990 J Molec Biol 403–410).

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software that can perform sequence comparisons include, but are not limited to, the BLAST package (Ausubel et al., 1995, *Short Protocols in Molecular Biology*, 3rd Edition, John Wiley & Sons), FASTA (Atschul et al., 1990, J. Mol. Biol., 403–410) and the GENEWORKS suite of comparison tools. Both BLAST and FASTA are available for offline and online searching (Ausubel et al., 1999 supra, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied. It is preferred to use the public default values for the GCG package, or in the case of other software, the default matrix, such as BLOSUM62.

Advantageously, the BLAST algorithm is employed, with parameters set to default values. The search parameters are defined as follows, and can be advantageously set to the defined default parameters.

Advantageously, "substantial identity" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (Karlin and Altschul 1990, *Proc. Natl. Acad. Sci. USA* 87:2264–68; Karlin and Altschul, 1993, *Proc. Natl. Acad. Sci. USA* 90:5873–7) with a few enhancements. The BLAST programs are tailored for sequence similarity searching, for example to identify homologues to a query sequence. For a discussion of basic issues in similarity searching of sequence databases, see Altschul et al (1994) Nature Genetics 6:119–129.

The five BLAST programs available at http://www.ncbi.nlm.nih.gov perform the following tasks:
blastp—compares an amino acid query sequence against a protein sequence database; blastn—compares a nucleotide query sequence against a nucleotide sequence database; blastx—compares the six-frame conceptual translation products of a nucleotide query sequence (both strands) against a protein sequence database; tblastn—compares a protein query sequence against a nucleotide sequence database dynamically translated in all six reading frames (both strands); tblastx—compares the six-frame translations of a nucleotide query sequence against the six-frame translations of a nucleotide sequence database.

BLAST uses the following search parameters:

HISTOGRAM—Display a histogram of scores for each search; default is yes. (See parameter H in the BLAST Manual).

DESCRIPTIONS—Restricts the number of short descriptions of matching sequences reported to the number specified; default limit is 100 descriptions. (See parameter V in the manual page).

EXPECT—The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF—Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTTOFF value. Higher CUTOFF values are more stringent, leading to fewer chance matches being reported. (See parameter S in the BLAST Manual). Typically, significance thresholds can be more intuitively managed using EXPECT.

ALIGNMENTS—Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

MATRIX—Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND—Restrict a TBLASTN search to just the top or bottom strand of the database sequences; or restrict a BLASTN, BLASTX or TBLASTX search to just reading frames on the top or bottom strand of the query sequence.

FILTER—Mask off segments of the query sequence that have low compositional complexity, as determined by the SEG program of Wootton & Federhen (1993) Computers and Chemistry 17:149–163, or segments consisting of short-periodicity internal repeats, as determined by the XNU program of Claverie & States (1993) Computers and Chemistry 17:191–201, or, for BLASTN, by the DUST program of Tatusov and Lipman. Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") and the letter "X" in protein sequences (e.g., "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi—Causes NCBI gi identifiers to be shown in the output, in addition to the accession and/or locus name.

Most preferably, sequence comparisons are conducted using the simple BLAST search algorithm. In some embodiments of the present invention, no gap penalties are used when determining sequence identity.

Hybridization

The present invention also encompasses nucleotide sequences that are capable of hybridizing to the sequences presented herein, or any fragment or derivative thereof, or to the complement of any of the above.

Hybridization means a "process by which a strand of nucleic acid joins with a complementary strand through base pairing" (Coombs J (1994) Dictionary of Biotechnology, Stockton Press, New York N.Y.) as well as the process of amplification as carried out in polymerase chain reaction technologies as described in Dieffenbach C W and G S Dveksler (1995, PCR Primer, a Laboratory Manual, Cold Spring Harbor Press, Plainview N.Y.).

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Nucleotide sequences of the invention capable of selectively hybridizing to the nucleotide sequences presented herein, or to their complement, will be generally at least 70%, preferably at least 75%, more preferably at least 85 or 90% and even more preferably at least 95% or 98% homologous to the corresponding nucleotide sequences presented herein over a region of at least 20, preferably at least 25 or 30, for instance at least 40, 60 or 100 or more contiguous nucleotides.

The term "selectively hybridizable" means that the nucleotide sequence used as a probe is used under conditions where a target nucleotide sequence of the invention is found to hybridize to the probe at a level significantly above background. The background hybridization may occur because of other nucleotide sequences present, for example, in the cDNA or genomic DNA library being screened. In this event, background implies a level of signal generated by interaction between the probe and a non-specific DNA member of the library which is less than 10 fold, and preferably less than 100 fold as intense as the specific interaction observed with the target DNA. The intensity of interaction may be measured, for example, by radiolabelling the probe, e.g. with $^{32}$P.

Also included within the scope of the present invention are nucleotide sequences that are capable of hybridizing to the nucleotide sequences presented herein under conditions of intermediate to maximal stringency. Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, maximum stringency hybridization can be used to identify or detect identical nucleotide sequences while an intermediate (or low) stringency hybridization can be used to identify or detect similar or related nucleotide sequences.

In a preferred embodiment, the present invention covers nucleotide sequences that can hybridize to one or more of the Tramell GPCR nucleotide sequences of the present invention under stringent conditions (e.g. 65° C. and 0.1× SSC {1×SSC=0.15 M NaCl, 0.015 M Na$_3$ Citrate pH 7.0). Where the nucleotide sequence of the invention is double-stranded, both strands of the duplex, either individually or in combination, are encompassed by the present invention. Where the nucleotide sequence is single-stranded, it is to be understood that the complementary sequence of that nucleotide sequence is also included within the scope of the present invention.

The present invention also encompasses nucleotide sequences that are capable of hybridizing to the sequences that are complementary to the sequences presented herein, or any fragment or derivative thereof. Likewise, the present invention encompasses nucleotide sequences that are complementary to sequences that are capable of hybridizing to the sequence of the present invention. These types of nucleotide sequences are examples of variant nucleotide sequences. In this respect, the term "variant" encompasses sequences that are complementary to sequences that are capable of hydridizing to the nucleotide sequences presented herein. Preferably, however, the term "variant" encompasses sequences that are complementary to sequences that are capable of hydridizing under stringent conditions (e.g., 65° C. and 0.1×SSC {1×SSC=0.15 M NaCl, 0.015 Na$_3$ citrate pH 7.0}) to the nucleotide sequences presented herein.

Cells

A cell that is useful according to the invention is preferably selected from the group consisting of bacterial cells, yeast cells, insect cells or mammal cells.

A cell that is useful according to the invention can be any cell into which a nucleic acid sequence encoding a receptor according to the invention can be introduced such that the receptor is expressed at natural levels or above natural levels, as defined herein. Preferably a receptor of the invention that is expressed in a cell exhibits normal or near normal pharmacology, as defined herein. Most preferably a receptor of the invention that is expressed in a cell comprises the nucleotide or amino acid sequence presented in FIG. 1 or a nucleotide or amino acid sequence that is at least 70% identical to the amino acid sequence presented in FIG. 1. Preferably, a receptor of the invention that is expressed in a cell will bind ADP with an affinity that is at least 100-fold, preferably 500-fold and most preferably 1000-fold greater than the affinity for IDP and UDP.

According to a preferred embodiment of the present invention, a cell is selected from the group consisting of COS7-cells, a CHO cell, a LM (TK–) cell, a NIH-3T3 cell, HEK-293 cell, K-562 cell or a 1321N1 astrocytoma cell but also other transfectable cell lines.

Assays for the Identification of Agents that Modulate the Activity of GPR86

Agents that modulate the activity of GPR86 can be identified in a number of ways that take advantage of the interaction of the receptor with ADP. For example. the ability to reconstitute GPR86/ADP binding either in vitro, on cultured cells or in vivo provides a target for the identification of agents that disrupt that binding. Assays based on disruption of binding can identify agents, such as small organic molecules, from libraries or collections of such molecules. Iternatively, such assays can identify agents in samples or extracts from natural sources, e.g., plant, fungal or bacterial extracts or even in human tissue samples (e.g., tumor tissue). In one aspect, the extracts can be made from cells expressing a library of variant nucleic acids, peptides or polypeptides. Modulators of GPR86/ADP binding can then be screened using a binding assay or a functional assay that measures downstream signalling through the receptor.

Another approach that uses the GPR86/ADP interaction more directly to identify agents that modulate GPR86 function measures changes in GPR86 downstream signalling induced by candidate agents or candidate modulators. These functional assays can be performed in isolated cell membrane fractions or on cells expressing the receptor on their surfaces.

The discovery that ADP is a ligand of the GPR86 receptor permits screening assays to identify agonists, antagonists and inverse agonists of receptor activity. The screening assays will have two general approaches.

1) Ligand binding assays, in which cells expressing GPR86, membrane extracts from such cells, or immobilized lipid membranes comprising GPR86 are exposed to labelled ADP and candidate compound. Following incubation, the reaction mixture is measured for specific binding of the labelled ADP to the GPR86 receptor. Compounds that interfere with binding or displace labelled ADP can be agonists, antagonists or inverse agonists of GPR86 activity. Subsequent functional analysis can then be performed on positive compounds to determine in which of these categories they belong.

2) Functional assays, in which a signalling activity of GPR86 is measured.

a) For agonist screening, cells expressing GPR86 or membranes prepared from them are incubated with a candidate compound, and a signalling activity of GPR86 is measured. The activity induced by compounds that modulate receptor activity is compared to that induced by ADP. An agonist or partial agonist will have a maximal biological activity corresponding to at least 10% of the maximal activity of ADP when the agonist or partial agonist is present at 10 nM or less, and preferably will have a potency which is at least as potent than ADP.

b) For antagonist or inverse agonist screening, cells expressing GPR86 or membranes isolated from them are assayed for signalling activity in the presence of ADP with or without a candidate compound. Antagonists will reduce the level of ADP-stimulated receptor activity by at least 10%, relative to reactions lacking the antagonist in the presence of ADP. Inverse agonists will reduce the constitutive activity of the receptor by at least 10%, relative to reactions lacking the inverse agonist.

c) For inverse agonist screening, cells expressing constitutive GPR86 activity or membranes isolated from them are used in a functional assay that measures an activity of the receptor in the presence of a candidate compound. Inverse agonists are those compounds that reduce the constitutive activity of the receptor by at least 10%. Overexpression of GPR86 may lead to constitutive activation. GPR86 can be overexpressed by placing it under the control of a strong constitutive promoter, e.g., the CMV early promoter. Alternatively, certain mutations of conserved GPCR amino acids or amino acid domains tend to lead to constitutive activity. See for example: Kjelsberg et al., 1992, J. Biol. Chem. 267:1430; McWhinney et al., 2000. J. Biol. Chem. 275:2087; Ren et al., 1993, J. Biol. Chem. 268:16483; Samama et al., 1993, J.Biol.Chem 268:4625; Parma et al., 1993, Nature 365:649; Parma et al., 1998, J. Pharmacol. Exp.Ther. 286:85; and Parent et al., 1996, J. Biol. Chem. 271:7949.

Ligand Binding and Displacement Assays:

One can use GPR86 polypeptides expressed on a cell, or isolated membranes containing receptor polypeptides, along with ADP in order to screen for compounds that inhibit the binding of ADP to GPR86. When identified in an assay that measures binding or ADP displacement alone, compounds will have to be subjected to functional testing to determine whether they act as agonists, antagonists or inverse agonists.

For displacement experiments, cells expressing a GPR86 polypeptide (generally 25,000 cells per assay or 1 to 100 μg of membrane extracts) are incubated in binding buffer with labelled ADP in the presence or absence of increasing concentrations of a candidate modulator. To validate and calibrate the assay, control competition reactions using increasing concentrations of unlabeled ADP can be performed. After incubation, cells are washed extensively, and bound, labelled ADP is measured as appropriate for the given label (e.g., scintillation counting, fluorescence, etc.). A decrease of at least 10% in the amount of labelled ADP bound in the presence of candidate modulator indicates displacement of binding by the candidate modulator. Candidate modulators are considered to bind specifically in this or other assays described herein if they displace 50% of labelled ADP (sub-saturating ADP dose) at a concentration of 10 nM or less.

Alternatively, binding or displacement of binding can be monitored by surface plasmon resonance (SPR). Surface plasmon resonance assays can be used as a quantitative method to measure binding between two molecules by the change in mass near an immobilized sensor caused by the binding or loss of binding of ADP from the aqueous phase to a GPR86 polypeptide immobilized in a membrane on the sensor. This change in mass is measured as resonance units versus time after injection or removal of the ADP or candidate modulator and is measured using a Biacore Biosensor (Biacore AB). GPR86 can be immobilized on a sensor chip (for example, research grade CM5 chip; Biacore AB) in a thin film lipid membrane according to methods described by Salamon et al. (Salamon et al., 1996, Biophys J. 71: 283–294; Salamon et al., 2001, Biophys. J. 80: 1557–1567; Salamon et al., 1999, Trends Biochem. Sci. 24: 213–219, each of which is incorporated herein by reference.). Sarrio et al. demonstrated that SPR can be used to detect ligand binding to the GPCR A(1) adenosine receptor immobilized in a lipid layer on the chip (Sarrio et al., 2000, Mol. Cell. Biol. 20: 5164–5174, incorporated herein by reference). Conditions for ADP binding to GPR86 in an SPR assay can be fine-tuned by one of skill in the art using the conditions reported by Sarrio et al. as a starting point.

SPR can assay for modulators of binding in at least two ways. First, ADP can be pre-bound to immobilized GPR86 polypeptide, followed by injection of candidate modulator at a concentration ranging from 0.1 nM to 1 µM. Displacement of the bound ADP can be quantitated, permitting detection of modulator binding. Alternatively, the membrane-bound GPR86 polypeptide can be pre-incubated with candidate modulator and challenged with ADP. A difference in ADP binding to the GPR86 exposed to modulator relative to that on a chip not pre-exposed to modulator will demonstrate binding or displacement of ADP in the presence of modulator. In either assay, a decrease of 10% or more in the amount of ADP bound is in the presence of candidate modulator, relative to the amount of a ADP bound in the absence of candidate modulator indicates that the candidate modulator inhibits the interaction of GPR86 and ADP.

Another method of detecting inhibition of binding of ADP to GPR86 uses fluorescence resonance energy transfer (FRET). FRET is a quantum mechanical phenomenon that occurs between a fluorescence donor (D) and a fluorescence acceptor (A) in close proximity to each other (usually <100 A of separation) if the emission spectrum of D overlaps with the excitation spectrum of A. The molecules to be tested, e.g. ADP and a GPR86 polypeptide, are labelled with a complementary pair of donor and acceptor fluorophores. While bound closely together by the GPR86:ADP interaction, the fluorescence emitted upon excitation of the donor fluorophore will have a different wavelength than that emitted in response to that excitation wavelength when the ADP and GPR86 polypeptide are not bound, providing for quantitation of bound versus unbound molecules by measurement of emission intensity at each wavelength. Donor fluorophores with which to label the GPR86 polypeptide are well known in the art. Of particular interest are variants of the A. victoria GFP known as Cyan FP (CFP, Donor (D)) and Yellow FP (YFP, Acceptor(A)). As an example, the YFP variant can be made as a fusion protein with GPR86. Vectors for the expression of GFP variants as fusions (Clontech) as well as flurophore-labeled ADP compounds (Molecular Probes) are known in the art. The addition of a candidate modulator to the mixture of labelled ADP and YFP-GPR86 protein will result in an inhibition of energy transfer evidenced by, for example, a decrease in YFP fluorescence relative to a sample without the candidate modulator. In an assay using FRET for the detection of GPR86:ADP interaction, a 10% or greater decrease in the intensity of fluorescent emission at the acceptor wavelength in samples containing a candidate modulator, relative to samples without the candidate modulator, indicates that the candidate modulator inhibits the GPR86:ADP interaction.

A variation on FRET uses fluorescence quenching to monitor molecular interactions. One molecule in the interacting pair can be labelled with a fluorophore, and the other with a molecule that quenches the fluorescence of the fluorophore when brought into close apposition with it. A change in fluorescence upon excitation is indicative of a change in the association of the molecules tagged with the fluorophore:quencher pair. Generally, an increase in fluorescence of the labelled GPR86 polypeptide is indicative that the ADP molecule bearing the quencher has been displaced. For quenching assays, a 10% or greater increase in the intensity of fluorescent emission in samples containing a candidate modulator; relative to samples without the candidate modulator, indicates that the candidate modulator inhibits GPR86:ADP interaction.

In addition to the surface plasmon resonance and FRET methods, fluorescence polarization measurement is useful to quantitate binding. The fluorescence polarization value for a fluorescently-tagged molecule depends on the rotational correlation time or tumbling rate. Complexes, such as those formed by GPR86 associating with a fluorescently labelled ADP, have higher polarization values than uncomplexed, labelled ADP. The inclusion of a candidate inhibitor of the GPR86:ADP interaction results in a decrease in fluorescence polarization, relative to a mixture without the candidate inhibitor, if the candidate inhibitor disrupts or inhibits the interaction of GPR86 with ADP. Fluorescence polarization is well suited for the identification of small molecules that disrupt the formation of receptor:ligand complexes. A decrease of 10% or more in fluorescence polarization in samples containing a candidate modulator, relative to fluorescence polarization in a sample lacking the candidate modulator, indicates that the candidate modulator inhibits GPR86:ADP interaction.

Another alternative for monitoring GPR86:ADP interactions uses a biosensor assay. ICS biosensors have been described in the art (Australian Membrane Biotechnology Research Institute; Cornell B, Braach-Maksvytis V, King L, Osman P, Raguse B, Wieczorek L, and Pace R. "A biosensor that uses ion-channel switches" Nature 1997, 387, 580). In this technology, the association of GPR86 and its ligand, is coupled to the closing of gramacidin-facilitated ion channels in suspended membrane bilayers and thus to a measurable change in the admittance (similar to impedance) of the biosensor. This approach is linear over six orders of magnitude of admittance change and is ideally suited for large scale, high throughput screening of small molecule combinatorial libraries. A 10% or greater change (increase or decrease) in admittance in a sample containing a candidate modulator, relative to the admittance of a sample lacking the candidate modulator, indicates that the candidate modulator inhibits the interaction of GPR86 and ADP. It is important to note that in assays testing the interaction of GPR86 with ADP, it is possible that a modulator of the interaction need not necessarily interact directly with the domain(s) of the proteins that physically interact with ADP. It is also possible that a modulator will iteract at a location removed from the site of interaction and cause, for example, a conformational change in the GPR86 polypeptide. Modulators (inhibitors or agonists) that act in this manner are nonetheless of interest as agents to modulate the activity of GPR86.

3. It should be understood that any of the binding assays described herein can be performed with a non-ADP ligand (for example, agonist, antagonist, etc.) of GPR86, e.g. a small molecule identified as described herein or ADP analogues including but not limited to any of the ADP analogues presented in U.S. Pat. No. 5,700,786, a natural or synthetic peptide, a polypeptide, an antibody or antigen-binding fragment thereof, a lipid, a carbohydrate, and a small organic molecule.

Any of the binding assays described can be used to determine the presence of an agent in a sample, e.g., a tissue sample, that binds to the GPR86 receptor molecule, or that affects the binding of ADP to the receptor. To do so, GPR86 polypeptide is reacted with ADP or another ligand in the presence or absence of the sample, and ADP or ligand binding is measured as appropriate for the binding assay being used. A decrease of 10% or more in the binding of ADP or other ligand indicates that the sample contains an agent that modulates ADP or ligand binding to the receptor polypeptide.

Functional Assays of Receptor Activity i. GTPase/GTP Binding Assays:

For GPCRs such as GPR86, a measure of receptor activity is the binding of GTP by cell membranes containing receptors. In the method described by Traynor and Nahorski, 1995, Mol. Pharmacol. 47: 848–854, incorporated herein by reference, one essentially measures G-protein coupling to membranes by detecting the binding of labelled GTP. For GTP binding assays, membranes isolated from cells expressing the receptor are incubated in a buffer containing 20 mM HEPES, pH 7.4, 100 mM NaCl, and 10 mM MgCl2, 80 pM $^{35}$S-GTPγS and 3 µM GDP. The assay mixture is incubated for 60 minutes at 30° C., after which unbound labelled GTP is removed by filtration onto GF/B filters. Bound, labelled GTP is measured by liquid scintillation counting. In order to assay for modulation of ADP-induced GPR86 activity, membranes prepared from cells expressing a GPR86 polypeptide are mixed with ADP, and the GTP binding assay is performed in the presence and absence of a candidate modulator of GPR86 activity. A decrease of 10% or more in labelled GTP binding as measured by scintillation counting in an assay of this kind containing a candidate modulator, relative to an assay without the modulator, indicates that the candidate modulator inhibits GPR86 activity. A similar GTP-binding assay can be performed without ADP to identify compounds that act as agonists. In this case, ADP-stimulated GTP binding is used as a standard. A compound is considered an agonist if it induces at least 50% of the level of GTP binding induced by ADP when the compound is present at 1 µM or less, and preferably will induce a level the same as or higher than that induced by ADP. GTPase activity is measured by incubating the membranes containing a GPR86 polypeptide with $γ^{32}$P-GTP. Active GTPase will release the label as inorganic phosphate, which is detected by separation of free inorganic phosphate in a 5% suspension of activated charcoal in 20 mM $H_3PO_4$, followed by scintillation counting. Controls include assays using membranes isolated from cells not expressing GPR86 (mock-transfected), in order to exclude possible non-specific effects of the candidate compound.

In order to assay for the effect of a candidate modulator on GPR86-regulated GTPase activity, membrane samples are incubated with ADP, with and without the modulator, followed by the GTPase assay. A change (increase or decrease) of 10% or more in the level of GTP binding or GTPase activity relative to samples without modulator is indicative of GPR86 modulation by a candidate modulator.

ii. Downstream Pathway Activation Assays:

a. Calcium Flux—the Aequorin-based Assay:

The aequorin assay takes advantage of the responsiveness of mitochondrial apoaequorin to intracellular calcium release induced by the activation of GPCRs (Stables et al., 1997, Anal. Biochem. 252:115–126; Detheux et al., 2000, J. Exp. Med., 192 1501–1508; both of which are incorporated herein by reference). Briefly, GPR86-expressing clones are transfected to coexpress mitochondrial apoaequorin and Gα16. Cells are incubated with 5 µM Coelenterazine H (Molecular Probes) for 4 hours at room temperature, washed in DMEM-F12 culture medium and resuspended at a concentration of $0.5×10^6$ cells/ml. Cells are then mixed with test agonist molecules and light emission by the aequorin is recorded with a luminometer for 30 sec. Results are expressed as Relative Light Units (RLU). Controls include assays using membranes isolated from cells not expressing GPR86 (mock transfected), in order to exclude possible non-specific effects of the candidate compound.

Aequorin activity or intracellular calcium levels are "changed" if light intensity increases or decreases by 10% or more in a sample of cells, expressing a GPR86 polypeptide and treated with a candidate modulator, relative to a sample of cells expressing the GPR86 polypeptide but not treated with the candidate modulator or relative to a sample of cells not expressing the GPR86 polypeptide (mock-transfected cells) but treated with the candidate modulator.

When performed in the absence of ADP, the assay can be used to identify an agonist of GPR86 activity. When the assay is performed in the presence of ADP, it can be used to assay for an antagonist.

b. Adenylate Cyclase Assay:

Assays for adenylate cyclase activity are described by Kenimer & Nirenberg, 1981, Mol. Pharmacol. 20: 585–591, incorporated herein by reference. That assay is a modification of the assay taught by Solomon et al., 1974, Anal. Biochem. 58: 541–548, also incorporated herein by reference. Briefly, 100 µl reactions contain 50 mM Tris-Hcl (pH 7.5), 5 mM $MgCl_2$, 20 mM creatine phosphate (disodium salt), 10 units (71 µg of protein) of creatine phosphokinase, 1 mM α-$^{32}$P-ATP (tetrasodium salt, 2 µCi), 0.5 mM cyclic AMP, G-$^3$H-labeled cyclic AMP (approximately 10,000 cpm), 0.5 mM Ro20-1724, 0.25% ethanol, and 50–200 µg of protein homogenate to be tested (i.e., homogenate from cells expressing or not expressing a GPR86 polypeptide, treated or not treated with ADP with or without a candidate modulator). Reaction mixtures are generally incubated at 37° C. for 6 minutes. Following incubation, reaction mixtures are deproteinized by the addition of 0.9 ml of cold 6% trichloroacetic acid. Tubes are centrifuged at 1800×g for 20 minutes and each supernatant solution is added to a Dowex AG50W-X4 column. The cAMP fraction from the column is eluted with 4 ml of 0.1 mM imidazole-HCl (pH 7.5) into a counting vial. Assays should be performed in triplicate. Control reactions should also be performed using protein homogenate from cells that do not express a GPR86 polypeptide.

According to the invention, adenylate cyclase activity is "changed" if it increases or decreases by 10% or more in a sample taken from cells treated with a candidate modulator of GPR86 activity, relative to a similar sample of cells not treated with the candidate modulator or relative to a sample of cells not expressing the GPR86 polypeptide (mock-transfected cells) but treated with the candidate modulator.

c. cAMP Assay:

Intracellular or extracellular cAMP is measured using a cAMP radioimmunoassay (RIA) or cAMP binding protein according to methods widely known in the art. For example, Horton & Baxendale, 1995, Methods Mol. Biol. 41: 91–105, which is incorporated herein by reference, describes an RIA for cAMP.

A number of kits for the measurement of cAMP are commercially available, such as the High Efficiency Fluorescence Polarization-based homogeneous assay marketed by LJL Biosystems and NEN Life Science Products. Control reactions should be performed using extracts of mock-transfected cells to exclude possible non-specific effects of some candidate modulators.

The level of cAMP is "changed" if the level of cAMP detected in cells, expressing a GPR86 polypeptide and treated with a candidate modulator of GPR86 activity (or in extracts of such cells), using the RIA-based assay of Horton & Baxendale, 1995, supra, increases or decreases by at least 10% relative to the cAMP level in similar cells not treated with the candidate modulator.

d. Phospholipid Breakdown, DAG Production and Inositol Triphosphate Levels:

Receptors that activate the breakdown of phospholipids can be monitored for changes due to the activity of known or suspected modulators of GPR86 by monitoring phospholipid breakdown, and the resulting production of second messengers DAG and/or inositol triphosphate ($IP_3$). Methods of detecting each of these are described in *Phospholipid Signalling Protocols*, edited by Ian M. Bird. Totowa, N.J., Humana Press, 1998, which is incorporated herein by reference. See also Rudolph et al., 1999, J. Biol. Chem. 274: 11824–11831, incorporated herein by reference, which also describes an assay for phosphatidylinositol breakdown. Assays should be performed using cells or extracts of cells expressing GPR86, treated or not treated with ADP with or without a candidate modulator. Control reactions should be performed using mock-transfected cells, or extracts from them in order to exclude possible non-specific effects of some candidate modulators.

According to the invention, phosphatidylinositol breakdown, and diacylglycerol and/or inositol triphosphate levels are "changed" if they increase or decrease by at least 10% in a sample from cells expressing a GPR86 polypeptide and treated with a candidate modulator, relative to the level observed in a sample from cells expressing a GPR86 polypeptide that is not treated with the candidate modulator.

e. PKC Activation Assays:

Growth factor receptor tyrosine kinases can signal via a pathway involving activation of Protein Kinase C (PKC), which is a family of phospholipid- and calcium-activated protein kinases. PKC activation ultimately results in the transcription of an array of proto-oncogene transcription factor-encoding genes, including c-fos, c-myc and c-jun, proteases, protease inhibitors, including collagenase type I and plasminogen activator inhibitor, and adhesion molecules, including intracellular adhesion molecule I (ICAM I). Assays designed to detect increases in gene products induced by PKC can be used to monitor PKC activation and thereby receptor activity. In addition, the activity of receptors that signal via PKC can be monitored through the use of reporter gene constructs driven by the control sequences of genes activated by PKC activation. This type of reporter gene-based assay is discussed in more detail below.

For a more direct measure of PKC activity, the method of Kikkawa et al., 1982, J. Biol. Chem. 257: 13341, incorporated herein by reference, can be used. This assay measures phosphorylation of a PKC substrate peptide, which is subsequently separated by binding to phosphocellulose paper. This PKC assay system can be used to measure activity of purified kinase, or the activity in crude cellular extracts. Protein kinase C sample can be diluted in 20 mM HEPES/ 2 mM DTT immediately prior to assay.

The substrate for the assay is the peptide Ac-FKKSFKL-NH2, derived from the myristoylated alanine-rich protein kinase C substrate protein (MARCKS). The $K_m$ of the enzyme for this peptide is approximately 50 µM. Other basic, protein kinase C-selective peptides known in the art can also be used, at a concentration of at least 2–3 times their $K_m$. Cofactors required for the assay include calcium, magnesium, ATP, phosphatidylserine and diacylglycerol. Depending upon the intent of the user, the assay can be performed to determine the amount of PKC present (activating conditions) or the amount of active PKC present (non-activating conditions). For most purposes according to the invention, non-activating activating conditions will be used, such that the PKC, that is active in the sample when it is isolated, is measured, rather than measuring the PKC that can be activated. For non-activating activating conditions, calcium is omitted from the assay in favor of EGTA.

The assay is performed in a mixture containing 20 mM HEPES, pH 7.4, 1–2 mM DTT, 5 mM $MgCl_2$, 100 µM ATP, ~1 µCi γ-$^{32}$P-ATP, 100 µg/ml peptide substrate (~100 µM), 140 µM/3.8 µM phosphatidylserine/diacylglycerol membranes, and 100 µM calcium (or 500 µM EGTA). 48 µl of sample, diluted in 20 mM HEPES, pH 7.4. 2 mM DTT is used in a final reaction volume of 80 µl. Reactions are performed at 30° C. for 5–10 minutes, followed by addition of 25 µl of 100 mM ATP, 100 mM EDTA, pH 8.0, which stops the reactions.

After the reaction is stopped, a portion (85 µl) of each reaction is spotted onto a Whatman P81 cellulose phosphate filter, followed by washes: four times 500 ml in 0.4% phosphoric acid, (5–10 min per wash); and a final wash in 500 ml 95% EtOH, for 2–5 min. Bound radioactivity is measured by scintillation counting. Specific activity (cpm/ nmol) of the labelled ATP is determined by spotting a sample of the reaction onto P81 paper and counting without washing. Units of PKC activity, defined as nmol phosphate transferred per min, are calculated as follows:

The activity, in UNITS (nmol/min) is:

$$= \frac{(cpm \text{ on paper}) \times (105 \text{ µl total}/85 \text{ µl spotted})}{(\text{assay time, min}) (\text{specific activity of } ATP \text{ } cpm/nmol)}.$$

An alternative assay can be performed using a Protein Kinase C Assay Kit sold by PanVera (Cat. #P2747).

Assays are περφορμεδ on extracts from cells expressing a GPR86 polypeptide, treated or not treated with ADP with or without a candidate modulator. Control reactions should be performed using mock-transfected cells, or extracts from them in order to exclude possible non-specific effects of some candidate modulators.

According to τηε invention, PKC activity is "changed" by a candidate modulator when the units of PKC measured by either assay described above increase or decrease by at least 10%, in extracts from cells expressing GPR86 and treated with a candidate modulator, relative to a reaction performed on a similar sample from cells not treated with a candidate modulator.

f. Kinase Assays:

MAP kinase activity can be assayed using any of several kits available commercially, for example, the p38 MAP Kinase assay kit sold by New England Biolabs (Cat #9820) or the FlashPlate™ MAP Kinase assays sold by Perkin-Elmer Life Sciences.

MAP Kinase activity is "changed" if the level of activity is increased or decreased by 10% or more in a sample from cells, expressing a GPR86 polypeptide, treated with a candidate modulator relative to MAP kinase activity in a sample from similar cells not treated with the candidate modulator.

Direct assays for tyrosine kinase activity using known synthetic or natural tyrosine kinase substrates and labelled phosphate are well known, as are similar assays for other types of kinases (e.g., Ser/Thr kinases). Kinase assays can be performed with both purified kinases and crude extracts prepared from cells expressing a GPR86 polypeptide, treated with or without ADP, with or without a candidate modulator. Control reactions should be performed using mock-transfected cells, or extracts from them in order to exclude possible non-specific effects of some candidate modulators. Substrates can be either full-length protein or synthetic peptides representing the substrate. Pinna & Ruzzene (1996, Biochem. Biophys. Acta 1314: 191–225, incorporated herein by reference) list a number of phosphorylation substrate sites useful for detecting kinase activities. A number of kinase substrate peptides are commercially available. One that is particularly useful is the "Src-related peptide," RRLIEDAEYAARG (available from Sigma #A7433), which is a substrate for many receptor and non-receptor tyrosine kinases. Because the assay described below requires binding of peptide substrates to filters, the peptide substrates should have a net positive charge to facilitate binding. Generally, peptide substrates should have at least 2 basic residues and a free-amino terminus. Reactions generally use a peptide concentration of 0.7–1.5 mM.

Assays are generally carried out in a 25 µl volume comprising 5 µl of 5×kinase buffer (5 mg/mL BSA, 150 mM Tris-Cl (pH 7.5), 100 mM $MgCl_2$; depending upon the exact kinase assayed for, $MnCl_2$ can be used in place of or in addition to the $MgCl_2$), 5 µl of 1.0 mM ATP (0.2 mM final concentration), γ-32P-ATP (100–500 cpm/pmol), 3 µl of 10 mM peptide substrate (1.2 mM final concentration), cell extract containing kinase to be tested (cell extracts used for kinase assays should contain a phosphatase inhibitor (e.g. 0.1–1 mM sodium orthovanadate)), and $H_2O$ to 25 µl. Reactions are performed at 30° C., and are initiated by the addition of the cell extract.

Kinase reactions are performed for 30 seconds to about 30 minutes, followed by the addition of 45 µl of ice-cold 10% trichloroacetic acid (TCA). Samples are spun for 2 minutes in a microcentrifuge, and 35 µl of the supernatant is spotted onto Whatman P81 cellulose phosphate filter circles. The filters are washed three times with 500 ml cold 0.5% phosphoric acid, followed by one wash with 200 ml of acetone at room temperature for 5 minutes. Filters are dried and incorporated $^{32}P$ is measured by scintillation counting. The specific activity of ATP in the kinase reaction (e.g., in cpm/pmol) is determined by spotting a small sample (2–5 µl) of the reaction onto a P81 filter circle and counting directly, without washing. Counts per minute obtained in the kinase reaction (minus blank) are then divided by the specific activity to determine the moles of phosphate transferred in the reaction.

Tyrosine kinase activity is "changed" if the level of kinase activity is increased or decreased by 10% or more in a sample from cells, expressing a GPR86 polypeptide, treated with a candidate modulator relative to kinase activity in a sample from similar cells not treated with the candidate modulator.

g. Transcriptional Reporters for Downstream Pathway Activation:

The intracellular signal initiated by binding of an agonist to a receptor, e.g., GPR86, sets in motion a cascade of intracellular events, the ultimate consequence of which is a rapid and detectable change in the transcription or translation of one or more genes. The activity of the receptor can therefore be monitored by detecting the expression of a reporter gene driven by control sequences responsive to GPR86 activation.

As used herein "promoter" refers to the transcriptional control elements necessary for receptor-mediated regulation of gene expression, including not only the basal promoter, but also any enhancers or transcription-factor binding sites necessary for receptor-regulated expression. By selecting promoters that are responsive to the intracellular signals resulting from agonist binding, and operatively linking the selected promoters to reporter genes whose transcription, translation or ultimate activity is readily detectable and measurable, the transcription based reporter assay provides a rapid indication of whether a given receptor is activated.

Reporter genes such as luciferase, CAT, GFP, β-lactamase or β-galactosidase are well known in the art, as are assays for the detection of their products.

Genes particularly well suited for monitoring receptor activity are the "immediate early" genes, which are rapidly induced, generally within minutes of contact between the receptor and the effector protein or ligand. The induction of immediate early gene transcription does not require the synthesis of new regulatory proteins. In addition to rapid responsiveness to ligand binding, characteristics of preferred genes useful for making reporter constructs include: low or undetectable expression in quiescent cells; induction that is transient and independent of new protein synthesis; subsequent shut-off of transcription requires new protein synthesis; and mRNAs transcribed from these genes have a short half-life. It is preferred, but not necessary that a transcriptional control element have all of these properties for it to be useful.

An example of a gene that is responsive to a number of different stimuli is the c-fos proto-oncogene. The c-fos gene is activated in a protein-synthesis-independent manner by growth factors, hormones, differentiation-specific agents, stress, and other known inducers of cell surface proteins. The induction of c-fos expression is extremely rapid, often occurring within minutes of receptor stimulation. This characteristic makes the c-fos regulatory regions particularly attractive for use as a reporter of receptor activation.

The c-fos regulatory elements include (see, Verma et al., 1987, Cell 51: 513–514): a TATA box that is required for transcription initiation; two upstream elements for basal transcription, and an enhancer, which includes an element with dyad symmetry and which is required for induction by TPA, serum, EGF, and PMA.

The 20 bp c-fos transcriptional enhancer element located between −317 and −298 bp upstream from the c-fos mRNA cap site, is essential for serum induction in serum starved NIH 3T3 cells. One of the two upstream elements is located at −63 to −57 and it resembles the consensus sequence for cAMP regulation.

The transcription factor CREB (cyclic AMP responsive element binding protein) is, as the name implies, responsive to levels of intracellular cAMP. Therefore, the activation of a receptor that signals via modulation of cAMP levels can be monitored by detecting either the binding of the transcription factor, or the expression of a reporter gene linked to a CREB-binding element (termed the CRE, or cAMP response element). The DNA sequence of the CRE is TGACGTCA. Reporter constructs responsive to CREB binding activity are described in U.S. Pat. No. 5,919,649.

Other promoters and transcriptional control elements, in addition to the c-fos elements and CREB-responsive constructs, include the vasoactive intestinal peptide (VIP) gene promoter (cAMP responsive; Fink et al., 1988, Proc. Natl. Acad. Sci. 85:6662–6666); the somatostatin gene promoter (cAMP responsive; Montminy et al., 1986, Proc. Natl. Acad. Sci. 8.3:6682–6686); the proenkephalin promoter (responsive to cAMP, nicotinic agonists, and phorbol esters; Comb et al., 1986, Nature 323:353–356); the phosphoenolpyruvate carboxy-kinase (PEPCK) gene promoter (cAMP responsive; Short et al., 1986, J. Biol. Chem. 261:9721–9726).

Additional examples of transcriptional control elements that are responsive to changes in GPCR activity include, but are not limited to those responsive to the AP-1 transcription factor and those responsive to NF-κB activity. The consensus AP-1 binding site is the palindrome TGA(C/G)TCA (Lee et al., 1987, Nature 325: 368–372; Lee et al., 1987, Cell 49: 741–752). The AP-1 site is also responsible for mediating induction by tumor promoters such as the phorbol ester 12-O-tetradecanoylphorbol-β-acetate (TPA), and are therefore sometimes also referred to as a TRE, for TPA-response element. AP-1 activates numerous genes that are involved in the early response of cells to growth stimuli. Examples of AP-1-responsive genes include, but are not limited to the genes for Fos and Jun (which proteins themselves make up AP-1 activity), Fos-related antigens (Fra) 1 and 2, IκBα, ornithine decarboxylase, and annexins I and II.

The NF-κB binding element has the consensus sequence GGGGACTTTCC (SEQ ID NO: 3). A large number of genes have been identified as NF-κB responsive, and their control elements can be linked to a reporter gene to monitor GPCR activity. A small sample of the genes responsive to NF-κB includes those encoding IL-1β (Hiscott et al., 1993, Mol. Cell. Biol. 13: 6231–6240), TNF-α (Shakhov et al., 1990, J. Exp. Med. 171: 35–47), CCR5 (Liu et al., 1998, AIDS Res. Hum. Retroviruses 14: 1509–1519), P-selection (Pan & McEver, 1995, J. Biol. Chem. 270: 23077–23083), Fas ligand (Matsui et al., 1998, J. Immunol. 161: 3469–3473), GM-CSF (Schreck & Baeuerle, 1990, Mol. Cell. Biol. 10: 1281–1286) and IκBα (Haskill et al., 1991, Cell 65: 1281–1289). Each of these references is incorporated herein by reference. Vectors encoding NF-κB-responsive reporters are also known in the art or can be readily made by one of skill in the art using, for example, synthetic NF-κB elements and a minimal promoter, or using the NF-κB-responsive sequences of a gene known to be subject to NF-κB regulation. Further, NF-κB responsive reporter constructs are commercially available from, for example, CLONTECH.

A given promoter construct should be tested by exposing GPR86-expressing cells, transfected with the construct, to ADP. An increase of at least two-fold in the expression of reporter in response to ADP indicates that the reporter is an indicator of GPR86 activity.

In order to assay GPR86 activity with an ADP responsive transcriptional reporter construct, cells that stably express a GPR86 polypeptide are stably transfected with the reporter construct. To screen for agonists, the cells are left untreated, exposed to candidate modulators, or exposed to ADP, and expression of the reporter is measured. The ADP-treated cultures serve as a standard for the level of transcription induced by a known agonist. An increase of at least 50% in reporter expression in the presence of a candidate modulator indicates that the candidate is a modulator of GPR86 activity. An agonist will induce at least as much, and preferably the same amount or more, reporter expression than ADP alone. This approach can also be used to screen for inverse agonists where cells express a GPR86 polypeptide at levels such that there is an elevated basal activity of the reporter in the absence of ADP or another agonist. A decrease in reporter activity of 10% or more in the presence of a candidate modulator, relative to its absence, indicates that the compound is an inverse agonist.

To screen for antagonists, the cells expressing GPR86 and carrying the reporter construct are exposed to ADP (or another agonist) in the presence and absence of candidate modulator. A decrease of 10% or more in reporter expression in the presence of candidate modulator, relative to the absence of the candidate modulator, indicates that the candidate is a modulator of GPR86 activity.

Controls for transcription assays include cells not expressing GPR86 but carrying the reporter construct, as well as cells with a promoterless reporter construct. Compounds that are identified as modulators of GPR86-regulated transcription should also be analyzed to determine whether they affect transcription driven by other regulatory sequences and by other receptors, in order to determine the specificity and spectrum of their activity.

The transcriptional reporter assay, and most cell-based assays, are well suited for screening expression libraries for proteins for those that modulate GPR86 activity. The libraries can be, for example, cDNA libraries from natural sources, e.g., plants, animals, bacteria, etc., or they can be libraries expressing randomly or systematically mutated variants of one or more polypeptides. Genomic libraries in viral vectors can also be used to express the mRNA content of one cell or tissue, in the different libraries used for screening of GPR86.

h) Inositol Phosphates (IP) Measurement:

Cells of the invention, for example, 1321N1 cells, are labelled for 24 hours with 10 μCi/ml [$^3$H] inositol in inositol free DMEM containing 5% FCS, antibiotics, amphotericin, sodium pyruvate and 400 μg/ml G418. Cells are incubated for 2 h in Krebs-Ringer Hepes (KRH) buffer of the following composition (124 mM NaCl, 5 mM KCl, 1.25 mM MgSO$_4$, 1.45 mM CaCl$_2$, 1.25 mM KH$_2$PO$_4$, 25 mM Hepes (pH:7.4) and 8 mM glucose). The cells are then challenged with various nucleotides for 30 s. The incubation is stopped by the addition of an ice cold 3% perchloric acid solution. IP are extracted and separated on Dowex columns as previously described (25). 2MeSATP and ATP solutions (1 mM) are treated at room temperature with 20 units/ml CPK and 10 Mm cp for 90 min to circumvent problems arising from the contamination and degradation of triphosphate nucleotide solutions.

GPR86 Assay

The invention provides for an assay for detecting the activity of a receptor of the invention in a sample. For example, GPR86 activity can be measured in a sample comprising a cell or a cell membrane that expresses GPR86. The assay is performed by incubating the sample in the presence or absence of ADP and carrying out a second messenger assay, as described above. The results of the second messenger assay performed in the presence or absence of ADP are compared to determine if the GPR86 receptor is active. An increase of 10% or more in the detected level of a given second messenger, as defined herein, in the presence of ADP relative to the amount detected in an assay performed in the absence of ADP is indicative of GPR86 activity.

Any of the assays of receptor activity, including but not limited to the GTP-binding, GTPase, adenylate cyclase, cAMP, phospholipid-breakdown, diacylglycerol, inositol triphosphate, arachidonic acid release (see below), PKC, kinase and transcriptional reporter assays, can be used to determine the presence of an agent in a sample, e.g., a tissue sample, that affects the activity of the GPR86 receptor molecule. To do so, GPR86 polypeptide is assayed for activity in the presence and absence of the sample or an extract of the sample. An increase in GPR86 activity in the presence of the sample or extract relative to the absence of the sample indicates that the sample contains an agonist of the receptor activity. A decrease in receptor activity in the presence of ADP or another agonist and the sample, relative to receptor activity in the presence of ADP alone, indicates that the sample contains an antagonist of GPR86 activity. If desired, samples can then be fractionated and further tested to isolate or purify the agonist or antagonist. The amount of increase or decrease in measured activity necessary for a sample to be said to contain a modulator depends upon the type of assay used. Generally, a 10% or greater change (increase or decrease) relative to an assay performed in the absence of a sample indicates the presence of a modulator in the sample. One exception is the transcriptional reporter assay, in which at least a two-fold increase or 10% decrease in signal is necessary for a sample to be said to contain a modulator. It is preferred that an agonist stimulates at least 50%, and preferably 75% or 100% or more, e.g., 2-fold, 5-fold, 10-fold or greater receptor activation than with ADP alone.

Other functional assays include, for example, microphysiometer or biosensor assays (see Hafner, 2000, Biosens. Bioelectron. 15: 149–158, incorporated herein by reference). The intracellular level of arachinoid acid can also be determined as described in Gijon et al., 2000, J. Biol. Chem., 275:20146–20156.

II. Diagnostic Assays Based upon the Interaction of GPR86 and ADP:

Signaling through GPCRs is instrumental in the pathology of a large number of diseases and disorders. GPR86, which is expressed in cells of the lymphocyte lineages, platelets, spleen as well as leukemic cells, can have a role in immune processes, cancer, thrombosis and associated disorders or diseases. The GPR86 expression pattern also includes the brain and further suggests a potential role as an ADP neurotransmitter.

The expression pattern of GPR86 and the knowledge with respect to disorders generally mediated by GPCRs suggests that GPR86 can be involved in disturbances of cell migration, cancer, development of tumours and tumour metastasis, inflammatory and neo-plastic processes, wound and bone healing and dysfunction of regulatory growth functions, diabetes, obesity, anorexia, bulimia, acute heart failure, hypotension, hypertension, urinary retention, osteoporosis, angina pectoris, myocardial infarction, restenosis, atherosclerosis, thrombosis and other cardiovascular diseases, autoimmune and inflammatory diseases, diseases characterized by excessive smooth muscle cell proliferation, aneurysms, diseases characterized by loss of smooth muscle cells or reduced smooth muscle cell proliferation, stroke, ischemia, ulcers, allergies, benign prostatic hypertrophy, migraine, vomiting, psychotic and neurological disorders, including anxiety, schizophrenia, manic depression, depression, delirium, dementia and severe mental retardation, degenerative diseases, neurodegenerative diseases such as Alzheimer's disease or Parkinson's disease, and dyskinasias, such as Huntington's disease or Gilles de la Tourett's syndrome and other related diseases including thrombosis and other cardiovascular diseases, autoimmune and inflammatory diseases.

The interaction of GPR86 with ADP can be used as the basis of assays for the diagnosis or monitoring of diseases, disorders or processes involving GPR86 signaling. Diagnostic assays for GPR86-related diseases or disorders can have several different forms. First, diagnostic assays can measure the amount of GPR86, genes or mRNA in a sample of tissue. Assays that measure the amount of mRNA encoding GPR86 polypeptide also fit into this category. Second, assays can evaluate the qualities of the receptor or the ligand. For example; assays that determine whether an individual expresses a mutant or variant form of GPR86 or a polypeptide ligand can be used diagnostically. Third, assays that measure one or more activities of GPR86 polypeptide can be used diagnostically.

A. Assays that Measure the Amount of GPR86

GPR86 levels can be measured and compared to standards in order to determine whether an abnormal level of the receptor or its ligand is present in a sample, either of which indicate probable dysregulation of GPR86 signaling. Polypeptide levels are measured, for example, by immunohistochemistry using antibodies specific for the polypeptide. A sample isolated from an individual suspected of suffering from a disease or disorder characterized by GPR86 activity is contacted with an antibody for GPR86, and binding of the antibody is measured as known in the art (e.g., by measurement of the activity of an enzyme conjugated to a secondary antibody).

Another approach to the measurement of GPR86 levels uses flow cytometry analysis of cells from an affected tissue. Methods of flow cytometry, including the fluorescent labeling of antibodies specific for GPR86, are well known in the art. Other approaches include radioimmunoassay or ELISA. Methods for each of these are also well known in the art.

The amount of binding detected is compared to the binding in a sample of similar tissue from a healthy individual, or from a site on the affected individual that is not so affected. An increase of 10% or more relative to the standard is diagnostic for a disease or disorder characterized by GPR86 dysregulation.

GPR86 expression can also be measured by determining the amount of mRNA encoding the polypeptides in a sample of tissue. Levels of mRNA can be measured by quantitative or semi-quantitative PCR. Methods of "quantitative" amplification are well known to those of skill in the art, and primer sequences for the amplification of both GPR86 are disclosed herein. A common method of quantitative PCR involves simultaneously co-amplyifying a known quantity of a control sequence using the same primers. This provides an internal standard that can be used to calibrate the PCR reaction. Detailed protocols for quantitative PCR are provided in PCR Protocols, A Guide to Methods and Applications, Innis et al., Academic Press, Inc. N.Y., (1990), which is incorporated herein by reference. An increase of 10% or more in the amount of mRNA encoding GPR86 in a sample, relative to the amount expressed in a sample of like tissue from a healthy individual or in a sample of tissue from an unaffected location in an affected individual is diagnostic for a disease or disorder characterized by dysregulation of GPR86 signaling.

B. Qualitative Assays

Assays that evaluate whether or not the GPR86 polypeptide or the mRNA encoding it are wild-type or not can be used diagnostically. In order to diagnose a disease or disorder characterized by GPR86 dysregulation in this manner, RNA isolated from a sample is used as a template for PCR amplification of GPR86. The amplified sequences are then either directly sequenced using standard methods, or are first cloned into a vector, followed by sequencing. A difference in the sequence that changes one or more encoded amino acids relative to the sequence of wild-type GPR86 can be diagnostic of a disease or disorder characterized by dysregulation of GPR86 signaling. It can be useful, when a change in coding sequence is identified in a sample, to express the variant receptor or ligand and compare its activity to that of wild type GPR86. Among other benefits, this approach can provide novel mutants, including constitutively active and null mutants.

In addition to standard sequencing methods, amplified sequences can be assayed for the presence of specific mutations using, for example, hybridization of molecular beacons that discriminate between wild type and variant sequences. Hybridization assays that discriminate on the basis of changes as small as one nucleotide are well known in the art. Alternatively, any of a number of "minisequencing" assays can be performed, including, those described, for example, in U.S. Pat. Nos. 5,888,819, 6,004,744 and 6,013,431 (incorporated herein by reference). These assays and others known in the art can determine the presence, in a given sample, of a nucleic acid with a known polymorphism.

If desired, array or microarray-based methods can be used to analyze the expression or the presence of mutation, in GPR86 sequences. Array-based methods for minisequencing and for quantitation of nucleic acid expression are well known in the art.

C. Functional Assays.

Diagnosis of a disease or disorder characterized by the dysregulation of GPR86 signaling can also be performed using functional assays. To do so, cell membranes or cell extracts prepared from a tissue sample are used in an assay of GPR86 activity as described herein (e.g., ligand binding assays, the GTP-binding assay, GTPase assay, adenylate cyclase assay, cAMP assay, arachidonic acid level, phospholipid breakdown, diacyl glycerol or inositol triphosphate assays, PKC activation assay, or kinase assay). The activity detected is compared to that in a standard sample taken from a healthy individual or from an unaffected site on the affected individual. As an alternative, a sample or extract of a sample can be applied to cells expressing GPR86, followed by measurement of GPR86 signaling activity relative to a standard sample. A difference of 10% or more in the activity measured in any of these assays, relative to the activity of the standard, is diagnostic for a disease or disorder characterized by dysregulation of GPR86 signaling.

Modulation of GPR86 Activity in a Cell According to the Invention

The discovery of ADP as a ligand of GPR86 provides methods of modulating the activity of a GPR86 polypeptide in a cell. GPR86 activity is modulated in a cell by delivering to that cell an agent that modulates the function of a GPR86 polypeptide. This modulation can be performed in cultured cells as part of an assay for the identification of additional modulating agents, or, for example, in an animal, including a human. Agents include ADP and its analogues as defined herein, as well as additional modulators identified using the screening methods described herein including but not limited to any of the ADP analogues presented in U.S. Pat. No. 5,700,786.

An agent can be delivered to a cell by adding it to culture medium. The amount to deliver will vary with the identity of the agent and with the purpose for which it is delivered. For example, in a culture assay to identify antagonists of GPR86 activity, one will preferably add an amount of ADP that half-maximally activates the receptors (e.g., approximately $EC_{50}$), preferably without exceeding the dose required for receptor saturation. This dose can be determined by titrating the amount of ADP to determine the point at which further addition of ADP has no additional effect on GPR86 activity.

When a modulator of GPR86 activity is administered to an animal for the treatment of a disease or disorder, the amount administered can be adjusted by one of skill in the art on the basis of the desired outcome. Successful treatment is achieved when one or more measurable aspects of the pathology (e.g., tumor cell growth, accumulation of inflammatory cells) is changed by at least 10% relative to the value for that aspect prior to treatment.

Candidate Modulators Useful According to the Invention

The invention provides for a compound that is a modulator of a receptor of the invention.

Preferably a candidate modulator is a nucleotide or a nucleotide which binds to a sugar, including but not limited to ADP-glucose or ADP-galactose. A candidate modulator may also be any ADP analog known in the art as well as any ligand that binds to the UDP glucose receptor.

The candidate compound may be a synthetic compound, or a mixture of compounds, or may be a natural product (e.g. a plant extract or culture supernatant). A candidate compound according to the invention includes a small molecule that can be synthesized, a natural extract, peptides, proteins, carbohydrates, lipids etc . . .

Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

Useful compounds may be found within numerous chemical classes. Useful compounds may be organic compounds, or small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

For primary screening, a useful concentration of a candidate compound according to the invention is from about 1 $\mu$M to about 60 $\mu$M or more (i.e., 100 $\mu$M, 1 mM, 10 mM, 100 mM, 1M etc . . . ). The primary screening concentration will be used as an upper limit, along with nine additional concentrations, wherein the additional concentrations are determined by reducing the primary screening concentration at half-log intervals (e.g. for 9 more concentrations) for secondary screens or for generating concentration curves.

Antibodies Useful According to the Invention

The invention provides for antibodies to GPR86. Antibodies can be made using standard protocols known in the art (See, for example, Antibodies: A Laboratory Manual ed. by Harlow and Lane (Cold Spring Harbor Press: 1988). A mammal, such as a mouse, hamster, or rabbit can be immunized with an immunogenic form of the peptide (e.g., GPR86 polypeptide or an antigenic fragment which is capable of eliciting an antibody response, or a fusion protein as described herein above). Immunogens for raising antibodies are prepared by mixing the polypeptides (e.g., isolated recombinant polypeptides or synthetic peptides) with adjuvants. Alternatively, GPR86 polypeptides or peptides are made as fusion proteins to larger immunogenic proteins. Polypeptides can also be covalently linked to other larger immunogenic proteins, such as keyhole limpet hemocyanin. Alternatively, plasmid or viral vectors encoding GPR86 polypeptide, or a fragment of these proteins, can be used to express the polypeptides and generate an immune response in an animal as described in Costagliola et al., 2000, J. Clin. Invest. 105:803–811, which is incorporated herein by reference. In order to raise antibodies, immunogens are typically administered intradermally, subcutaneously, or intramuscularly to experimental animals such as rabbits, sheep, and mice. In addition to the antibodies discussed above, genetically engineered antibody derivatives can be made, such as single chain antibodies.

The progress of immunization can be monitored by detection of antibody titers in plasma or serum. Standard ELISA, flow cytometry or other immunoassays can also be used with the immunogen as antigen to assess the levels of antibodies. Antibody preparations can be simply serum from an immunized animal, or if desired, polyclonal antibodies can be isolated from the serum by, for example, affinity chromatography using immobilized immunogen.

To produce monoclonal antibodies, antibody-producing splenocytes can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495–497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with GPR86 polypeptide, and monoclonal antibodies isolated from the media of a culture comprising such hybridoma cells.

High Throughput Screening Kit

A high throughput screening kit according to the invention comprises all the necessary means and media for performing the detection of a modulator compound including an agonist, antagonist, inverse agonist or inhibitor to the receptor of the invention in the presence of ADP, preferably at a concentration in the range of 1 nM to 10 $\mu$M. The kit comprises the following successive steps. Recombinant cells of the invention, comprising and expressing the nucleotide sequence encoding the GPR86 (P2Y$_{13}$) receptor, are grown on a solid support, such as a microtiter plate, more preferably a 96 well microtiter plate, according to methods well known to the person skilled in the art especially as described in WO 00/02045. Modulator compounds according to the invention, at concentrations from about 1 nM to 10 $\mu$M or more, are added to the culture media of defined wells in the presence of an appropriate concentration of ADP (preferably in the range of 1 nM to 1 $\mu$M).

Secondary messenger assays, amenable to high throughput screening analysis, are performed including but not limited to the measurement of intracellular levels of cAMP, intracellular inositol phosphate, intracellular diacylglycerol concentrations, arachinoid acid concentration or MAP kinase or tyrosine kinase activity (as decribed above). For example, the GPR86 activity, as measured in a cyclic AMP assay, is quantified by a radioimmunoassay as previously described (26). Results are compared to the baseline level of GPR86 activity obtained from recombinant cells according to the invention in the presence of ADP but in the absence of added modulator compound. Wells showing at least 2 fold, preferably 5 fold, more preferably 10 fold and most preferably a 100 fold or more increase or decrease in GPR86 activity as compared to the level of activity in the absence of modulator, are selected for further analysis.

Other Kits Useful According to the Invention

The invention provides for kits useful for screening for modulators of GPR86 activity, as well as kits useful for diagnosis of diseases or disorders characterized by dysregulation of GPR 86 signaling. Kits useful according to the invention can include an isolated GPR86 polypeptide (including a membrane-or cell-associated GPR86 polypeptide, e.g., on isolated membranes, cells expressing GPR86, or, on an SPR chip). A kit can also comprise an antibody specific for GPR86. Alternatively, or in addition, a kit can contain cells transformed to express GPR86 polypeptide. In a further embodiment, a kit according to the invention can contain a polynucleotide encoding a GPR86 polypeptide. In a still further embodiment, a kit according to the invention may comprise the specific primers useful for amplification of GPR86 as described below. All kits according to the invention will comprise the stated items or combinations of items and packaging materials therefore. Kits will also include instructions for use.

Transgenic Animals

Transgenic mice provide a useful tool for genetic and developmental biology studies and for the determination of the function of a novel sequence. According to the method of conventional transgenesis, additional copies of normal or modified genes are injected into the male pronucleus of the zygote and become integrated into the genomic DNA of the recipient mouse. The transgene is transmitted in a Mendelian manner in established transgenic strains. Constructs useful for creating transgenic animals comprise genes under the control of either their normal promoters or an inducible promoter, reporter genes under the control of promoters to be analyzed with respect to their patterns of tissue expression and regulation, and constructs containing dominant mutations, mutant promoters, and artificial fusion genes to be studied with regard to their specific developmental outcome. Typically, DNA fragments on the order of 10 kilobases or less are used to construct a transgenic animal (Reeves, 1998, New. Anat., 253:19). Transgenic animals can be created with a construct comprising a candidate gene containing one or more polymorphisms according to the invention. Alternatively, a transgenic animal expressing a candidate gene containing a single polymorphism can be crossed to a second transgenic animal expressing a candidate gene containing a different polymorphism and the combined effects of the two polymorphisms can be studied in the offspring animals.

Other Transgenic Animals

The invention provides for transgenic animals that include but are not limited to transgenic mice, rabbits, rats, pigs, sheep, horses, cows, goats, etc. A protocol for the production of a transgenic pig can be found in White and Yannoutsos, Current Topics in Complement Research: 64$^{th}$ Forum in Immunology, pp. 88–94; U.S. Pat. Nos. 5,523,226; 5,573, 933: PCT Application WO93/25071; and PCT Application WO95/04744. A protocol for the production of a transgenic mouse can be found in U.S. Pat. No. 5,530,177. A protocol for the production of a transgenic rat can be found in Bader and Ganten, Clinical and Experimental Pharmacology and Physiology, Supp. 3:S81–S87, 1996. A protocol for the production of a transgenic cow can be found in Transgenic Animal Technology, A Handbook, 1994, ed., Carl A. Pinkert, Academic Press, Inc. A protocol for the production of a transgenic rabbit can be found in Hammer et al., Nature 315:680–683, 1985 and Taylor and Fan, Frontiers in Bioscience 2:d298–308, 1997.

Knock Out Animals i. Standard

Knock out animals are produced by the method of creating gene deletions with homologous recombination. This technique is based on the development of embryonic stem (ES) cells that are derived from embryos, are maintained in culture and have the capacity to participate in the development of every tissue in the mouse when introduced into a host blastocyst. A knock out animal is produced by directing homologous recombination to a specific target gene in the ES cells, thereby producing a null allele of the gene. The potential phenotypic consequences of this null allele (either in heterozygous or homozygous offspring) can be analyzed (Reeves, supra).

ii. In vivo Tissue Specific Knock Out in Mice Using Cre-lox.

The method of targeted homologous recombination has been improved by the development of a system for site-specific recombination based on the bacteriophage P1 site specific recombinase Cre. The Cre-loxP site-specific DNA recombinase from bacteriophage P1 is used in transgenic mouse assays in order to create gene knockouts restricted to defined tissues or developmental stages. Regionally restricted genetic deletion, as opposed to global gene knockout, has the advantage that a phenotype can be attributed to a particular cell/tissue (Marth, 1996, *Clin. Invest.* 97: 1999). In the Cre-loxP system one transgenic mouse strain is engineered such that loxP sites flank one or more exons of the gene of interest. Homozygotes for this so called 'floxed gene' are crossed with a second transgenic mouse that expresses the Cre gene under control of a cell/tissue type transcriptional promoter. Cre protein then excises DNA between loxP recognition sequences and effectively removes target gene function (Sauer, 1998, *Methods,* 14:381). There are now many in vivo examples of this method, including the inducible inactivation of mammary tissue specific genes (Wagner et al., 1997, *Nucleic Acids Res.,* 25:4323).

iii. Bac Rescue of Knock Out Phenotype

In order to verify that a particular genetic polymorphism/mutation is responsible for altered protein function in vivo one can "rescue" the altered protein function by introducing a wild-type copy of the gene in question. In vivo complementation with bacterial artificial chromosome (BAC) clones expressed in transgenic mice can be used for these purposes. This method has been used for the identification of the mouse circadian Clock gene (Antoch et al., 1997, *Cell* 89: 655).

Materials

Tryp-sin was from Flow Laboratories (Bioggio, Switzerland). Culture media, G418, fetal bovine serum (FBS), restriction enzymes, Platinum Pfx and Taq DNA polymerases were purchased from Life Technologies, Inc. (Merelbeke, Belgium). The radioactive product myo-D-[2-$^3$H]inositol (17.7 Ci/mmol) was from Amersham (Ghent, Belgium). Dowex AG1X8 (formate form) was from Bio-Rad Laboratories (Richmond, Calif.). ATP, ADP, adenoside, ADPβS (adenosine 5'-O-(2-thiodiphosphate)), A2P5P (adenosine 2',5'-diphosphate), A3P5P (adenosine 3',5'-diphosphate), A3P5PS (adenosine 3'-phosphate 5'-phosphosulfate), UTP, UDP, ITP, IDP, UDP-glucose and 3-isobutyl-1-methyl-xanthine (IBMX) were obtained from Sigma Chemical Co. (St. Louis, Mo.). 2-methylthio-ADP (2MeSADP) and 2-methylthio-ATP (2MeSATP) were from Research Biochemicals International (Natick, Mass.). Forskolin was purchased from Calbiochem. (Bierges, Belgium). Rolipram was a gift from the Laboratories Jacques Logeais (Trappes, France). pEFIN5 is an expression vector developed by Euroscreen (Brussels, Belgium). Monoclonal antibody specific for the dually phosphorylated forms of Erk1 and Erk2 (at Thr$^{202}$ and Tyr$^{204}$) was obtained from New England Biolabs (Beverly, Mass.).

Dosage and Mode of Administration

By way of example, a patient can be treated as follows by the administration of a modulator of GPR86 (for example, an agonist, antagonist or inhibitor of GPR86, of the invention). A modulator of GPR86 the invention can be administered to the patient, preferably in a biologically compatible solution or a pharmaceutically acceptable delivery vehicle, by ingestion, injection, inhalation or any number of other methods. The dosages administered will vary from patient to patient; a "therapeutically effective dose" can be determined, for example but not limited to, by the level of enhancement of function (e.g., as determined in a second messenger assay described herein). Monitoring ADP binding will also enable one skilled in the art to select and adjust the dosages administered. The dosage of a modulator of GPR86 of the invention may be repeated daily, weekly, monthly, yearly, or as considered appropriate by the treating physician.

Pharmaceutical Compositions

The invention provides for compositions comprising a GPR86 modulator according to the invention admixed with a physiologically compatible carrier. As used herein, "physiologically compatible carrier" refers to a physiologically acceptable diluent such as water, phosphate buffered saline, or saline, and further may include an adjuvant. Adjuvants such as incomplete Freund's adjuvant, aluminium phosphate, aluminium hydroxide, or alum are, materials well known in the art.

The invention also provides for pharmaceutical compositions. In addition to the active ingredients these pharmaceutical compositions may contain suitable pharmaceutically acceptable carrier preparations which can be used pharmaceutically.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated are used in the formulation. Such penetrants are generally known in the art.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc . . . Salts tend to be more soluble in aqueous or other protonic solvents that are the corresponding free base forms. In other cases, the preferred preparation may be a lyophilized powder in 1 mM-50 mM histidine, 0.1%–2% sucrose, 2%–7% mannitol at a Ph range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition with information including amount, frequency and method of administration.

EXAMPLES

The invention is illustrated by the following nonlimiting examples wherein the following materials and methods are employed. The entire disclosure of each of the literature references cited hereinafter are incorporated by reference herein.

Example 1

Cloning and Sequencing

An intronless coding sequence encoding a novel receptor strongly related to the human $P2Y_{12}$ receptor was identified on the genomic clone RP11-25K24 (GenBank accession AC024886) located in the 3q24 region and in the following patent: WO 00/31258; ARENA; sequence number 18.

Specific oligonucleotide primers were synthesized on the basis of the sequence of the GPR86 human receptor: a sense primer 5'-CCGGAATTCACCATGAACACCACAGTG-ATGC-3' (SEQ ID NO: 4) and an antisense primer 5'-CTTGTCTAGATCAGCCTAAGGTTATGTTGTC-3' (SEQ ID NO:) A polymerase chain reaction (PCR) was performed on three different spleen cDNAs using the Platinum Pfx DNA Polymerase. The amplification conditions were as follows: 94° C., 15 s; 50° C., 30 s; 68° C., 2 min for 35 cycles. Amplifications resulted in a fragment of 1 kilobase containing the entire coding sequence of the GPR86 gene. The coding sequence was then subcloned between the EcoRI and XbaI sites of the bicistronic pEFIN5 expression vector and sequenced on both strands for each of the three cDNAs using the BigDye Terminator cycle sequencing kit (Applied Biosystems, Warrington, Great Britain).

This 1002 base pairs (bp)-open reading frame was also identified recently by Wittenberger et al. (GenBank accession AF295368) and reported to encode an orphan G-protein-coupled receptor that they called GPR86 (24). The start codon is preceded by a stop codon 18 bp upstream. Oligonucleotide primers were synthesized on the basis of this coding sequence. They were used in PCR starting from spleen cDNA. A PCR product with a size compatible with GPR86 coding sequence was inserted into the pEFIN5 expression vector and sequenced on both strands (FIG. 1). The putative membrane-spanning domains are underlined and numbered I to VII. The putative sites of phosphorylation by protein kinase A or by protein kinase C are indicated respectively by a black circle (●) or a black diamond (♦). The potential N-glycosylation sites are indicated by a black square (■).

The sequence obtained matched perfectly to the sequence of Wittenberger et al. amplified from human cDNA libraries from fetal brain and placenta. The 1002 bp-open reading frame starts with an ATG-codon in a Kozak consensus and encodes a protein of 333 amino acids. The peptidic sequence contains three potential sites for N-linked glycosylation (two in the extracellular N-terminal part ($N^2$ and $N^{10}$) and one in the third extracellular loop ($N^{264}$), two potential sites for phosphorylation by protein kinase C (one in the third intracellular loop ($S^{217}$) and one in the carboxyterminal part ($T^{304}$)) and one by protein kinase A (in the carboxyterminal part ($T^{316}$)) (FIG. 1). The novel receptor displays a significant homology with the human $P2Y_{12}$ and UDP-glucose receptors (FIG. 2), 48% and 45% amino acid identity respectively. The similarity with the other P2Y receptors is much lower (FIG. 2), for example, 25% and 26% amino acid identity with respectively the human $P2Y_1$ and $P2Y_2$ receptors. Alignment of the amino acid sequence of GPR86 ($P2Y_{13}$) with purinergic receptors (P2Y1,-2,-4,-6,-1,-12), UDP glucose receptor and other purinergic related sequences (GPR17, GPR87, H963) were performed using ClustalX algorithm. Then, the dendrogram was constructed using TreeView algorithm.

Example 2

Tissue Distribution of GPR86 Human Receptor

Figure 3A:
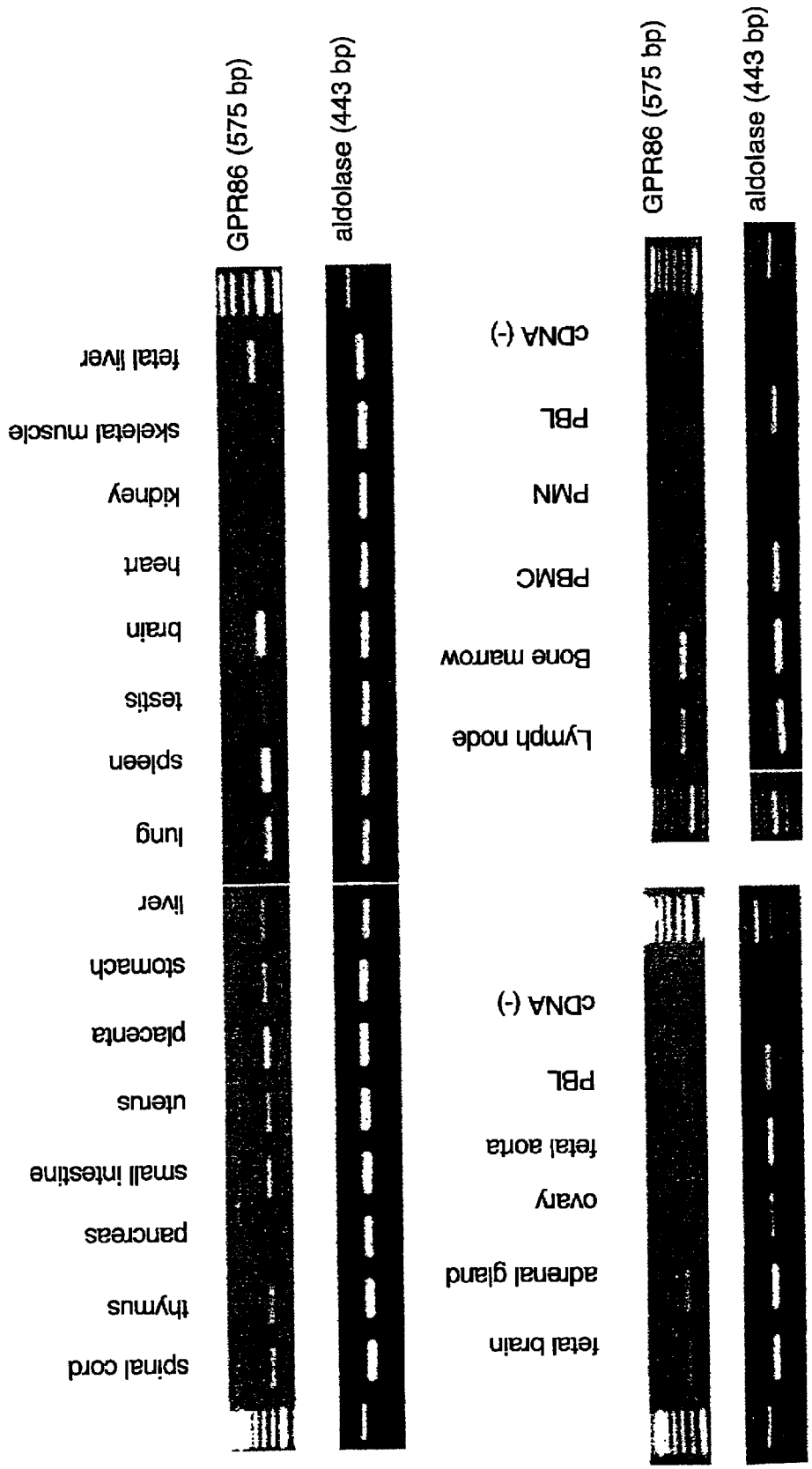
FIGS. 3A and 3B represent tissue distribution of the human GPR86 ($P2Y_{13}$) receptor.

GPR86 mRNA was amplified by RT-PCR in several human tissues (FIG. 3A).

Reverse transcription-polymerase chain reaction (RT-PCR) experiments were carried out using a panel of polyA+ RNA (Clontech). The GPR86 primers were as follows GPR86 sense primer (5'-TGTGTCGTTTTTCTTCGGTG-3') (SEQ ID NO: 6') and GPR86 antisense primer (5'-CTGCCAAAAAGAGAGTTG-3') (SEQ ID NO: 7). The expected size of the amplified DNA band was 575 bp. Two primers synthesized on the basis of aldolase coding sequence were used as controls to produce a product with an expected size of 443 bp: aldolase sense primer 5'-GGCAAGGGCATCCTGGCTGC-3' (SEQ ID NO: 8) and aldolase antisense reverse 5'-TAACGGGCCAGAA-CATTGGCATT-3' (SEQ ID NO: 9). Approximately 75 ng of poly A+RNA was reverse transcribed with Superscript II (Life Technologies, Inc., Merelbeke, Belgium) and used for PCR. PCR was performed using the Taq polymerase under the following conditions: denaturation at 94° C. for 3 min, 38 cycles at 94° C. for 1 min, 58° C. for 2 min and 72° C. for 2 min. Aliquots (10 μl) of the PCR reaction were analysed by 1% agarose gel electrophoresis.

Figure 3B:
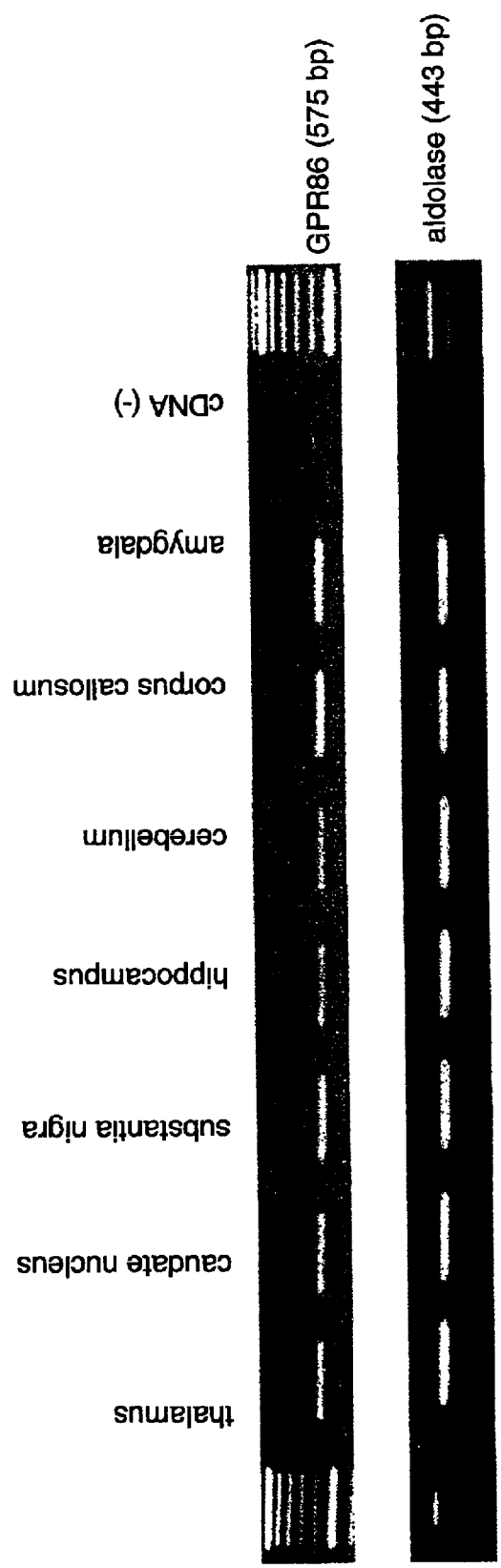

RT-PCR experiments were carried out using a panel of polyA+ RNA (Clontech) and specific primers of GPR86 sequence. The expected size of the amplified GPR86 and aldolase bands were respectively 575 and 443 bp. cDNA(−) indicates the negative control of the PCR reaction without cDNA template. Aliquots (10 μl) of the PCR reaction were analysed by 1% agarose gel electrophoresis. A strong band of the expected size (575 bp) was detected in spleen and brain (adult), and at lower intensity in placenta, lung, liver, spinal cord, thymus, small intestine, uterus, stomach, testis, fetal brain, and adrenal gland, but not in pancreas, heart, kidney, skeletal muscle, ovary, fetal aorta or the negative control without cDNA (FIG. 3A). A 575 bp-band was also clearly detected in lymph node and bone marrow, and weakly detected in peripheral blood mononuclear cells (PBMC) (FIG. 3A). No signal was detected in peripheral blood lymphocytes (PBL) and polymorphonuclear cells (PMN) (FIG. 3A). GPR86 messengers were detected in different brain regions (thalamus, caudate nucleus, substantia nigra, hippocampus, cerebellum, corpus callosum and amygdala) (FIG. 3B). The amplification of a fragment of aldolase coding sequence was used as control.

Northern blot analysis with hGPR86 revealed a strong 2.9 kb transcript in spleen and a weaker one in liver, placenta, leukocytes, and brain. Evaluation of the expression of hGPR86 in different brain regions revealed the 2.9 kb transcript as a strong signal in substantia nigra, thalamus, and medulla, less strong in frontal and temporal lobe, putamen, amygdala, caudate nucleus, hippocampus, spinal cord, corpus callosum, and weak in cerebellum and occipital lobe. The transcript was not detectable in the cerebral cortex. The wide spread expression of hGPR86 shown in the Northern blot analysis is reflected by the origin of 16 EST sequences found for this GPCR in the public database, derived from diverse tissues as germ cell tumors, fetal liver, fetal spleen, colon, pregnant uterus and multiple sclerosis lesions. The PCR amplification of hGPR86 from brain and placenta cDNAs is also in agreement with these results (24).

Example 3

Stable Expression of the Novel Receptor in 1321N1 Astrocytoma Cells

The complete sequence of the novel receptor was introduced in the pEFIN5 expression vector in order to transfect the 1321N1 astrocytoma cell line, used previously to characterize several P2Y subtypes (5, 13, 14). 1321N1 astrocytoma cells expressing G□$_{16}$ protein were transfected with the recombinant GPR86-pEFIN5 plasmid or with the plasmid alone.

CHO-K1 and 1321N1 cells were transfected with the recombinant GPR86-pEFIN5 plasmid or with the plasmid alone using the FuGENE™6 transfection reagent (Roche Molecular Biochemicals). A clone called AG32 corresponding to 1321N1 cells previously transfected with pERAEQ2 plasmid encoding Gα$_{16}$ (provided by Euroscreen), was transfected. The CHO-K$_1$ and 1321N1 transfected cells were selected with 400 μg/ml G418 in complete medium (10% FBS, 100 units/ml penicillin, 100 μg/ml streptomycin and 2:5 μg/ml amphotericin B in respectively Ham's F12 or DMEM (Dulbecco's modified Eagle's) medium) two days after transfection and maintained in the same medium. The AG32 cells were maintained in the same DMEM complete medium supplemented with 500 μg/ml zeocin.

The pool of G418-resistant clones was tested for its functional IP$_3$ response to several nucleotides, according to the method described above. The cells were challenged by various nucleotides at a concentration of 100 μM for 30 s: ATP, ADP, UTP, UDP, ITP, IDP, TDP. No response was obtained in 1321N1 cells expressing GPR86 receptor alone, while a strong IP$_3$ response to histamine was observed in these cells, but ADP, UDP and IDP induced an IP$_3$ response in 1321N1 cells expressing both GPR86 receptor and Gα$_{16}$ protein. No IP$_3$ response was observed for the other nucleotides, except for ATP and 2MeSATP, but these responses were lost after HPLC-purification (data not shown). No IP$_3$ response was observed in response to any nucleotide in 1321N1 or 1321N1-Gα$_{16}$ cells transfected with the wild-type pEFIN5 vector and used as negative control.

Figure 4A:
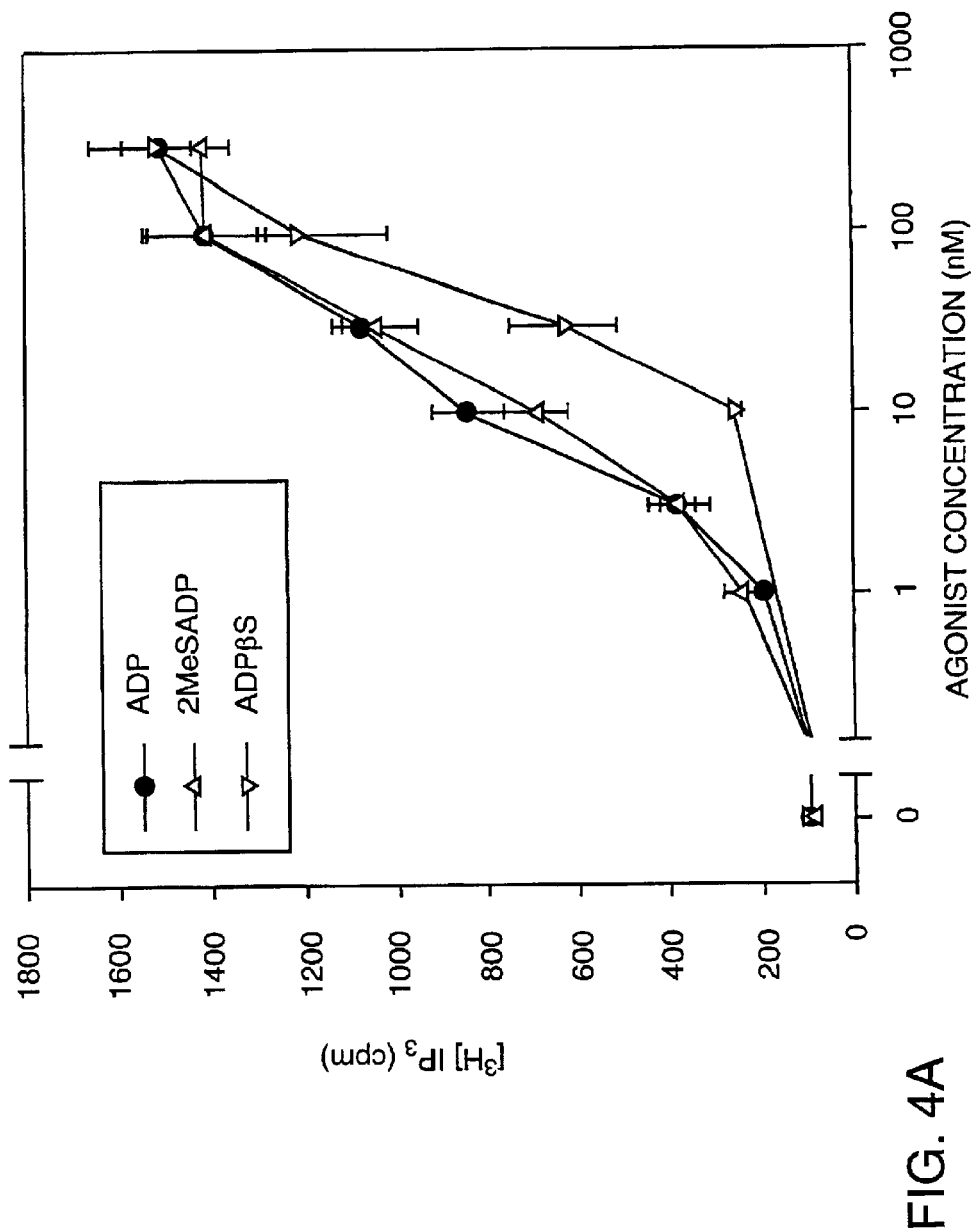
FIGS. 4A to 4C represent respectively:
concentration-action curves of ADP, 2MeSADP and ADPβS on $IP_3$ accumulation in 1321N1-Gα16 cells expressing the GPR86 ($P2Y_{13}$) human receptor;
agonistic effects of ADP, ATP and 2MeSATP on $IP_3$ accumulation in 1321N1 cells expressing the GPR86 ($P2Y_{13}$) human receptor together with $G\alpha_{16}$, and;
the effect of pertussis toxin on $IP_3$ accumulation induced by ADP on 1321N1 cells expressing the GPR86 human receptor together with $G\alpha_{16}$.

In 1321N1 cells expressing both GPR86 receptor and the Gα$_{16}$, concentration-action curves were established for ADP, IDP and UDP and revealed the strong affinity of GPR86 for ADP. The following range of potency was obtained: ADP>>>IDP>UDP. The affinity of GPR86 for ADP was approximately one thousand-fold greater than that of IDP and UDP. Concentration-action curves for ADP, 2MeSADP and ADPβS. The following EC$_{50}$ values were computed respectively for ADP, 2MeSADP and ADPβS were obtained: 11.4±2.2 nM, 14.2±3.0 nM and 48.4±0.4 nM (mean±S.D. of three independent experiments) (FIG. 4A). 1321N1 transfected cells were incubated in the presence of various concentrations of ADP, 2MeSADP and ADPβS for 30 s. The data represent the mean±S.D. of triplicate experimental points obtained in one representative experiment of three. No IP$_3$ response was obtained for A2P5P (ADP 2',5'-diphosphate), A3P5P (adenosine 3',5'-diphosphate) and A3P5PS (adenosine 3'-phosphate 5'-phosphosulfate).

Effects of 2MeSATP and ATP were obtained at concentrations higher than for the respective diphosphates nucleotides (FIG. 4B). 1321N1 transfected cells were pre-incubated with or without 100 ng/ml pertussis toxin for 18 h and then incubated in the presence of ADP (300 nM) or water (CONT) for 30 s. The data represent the mean±S.D. of triplicate experimental points obtained in one representative experiment of two.

Figure 4B:
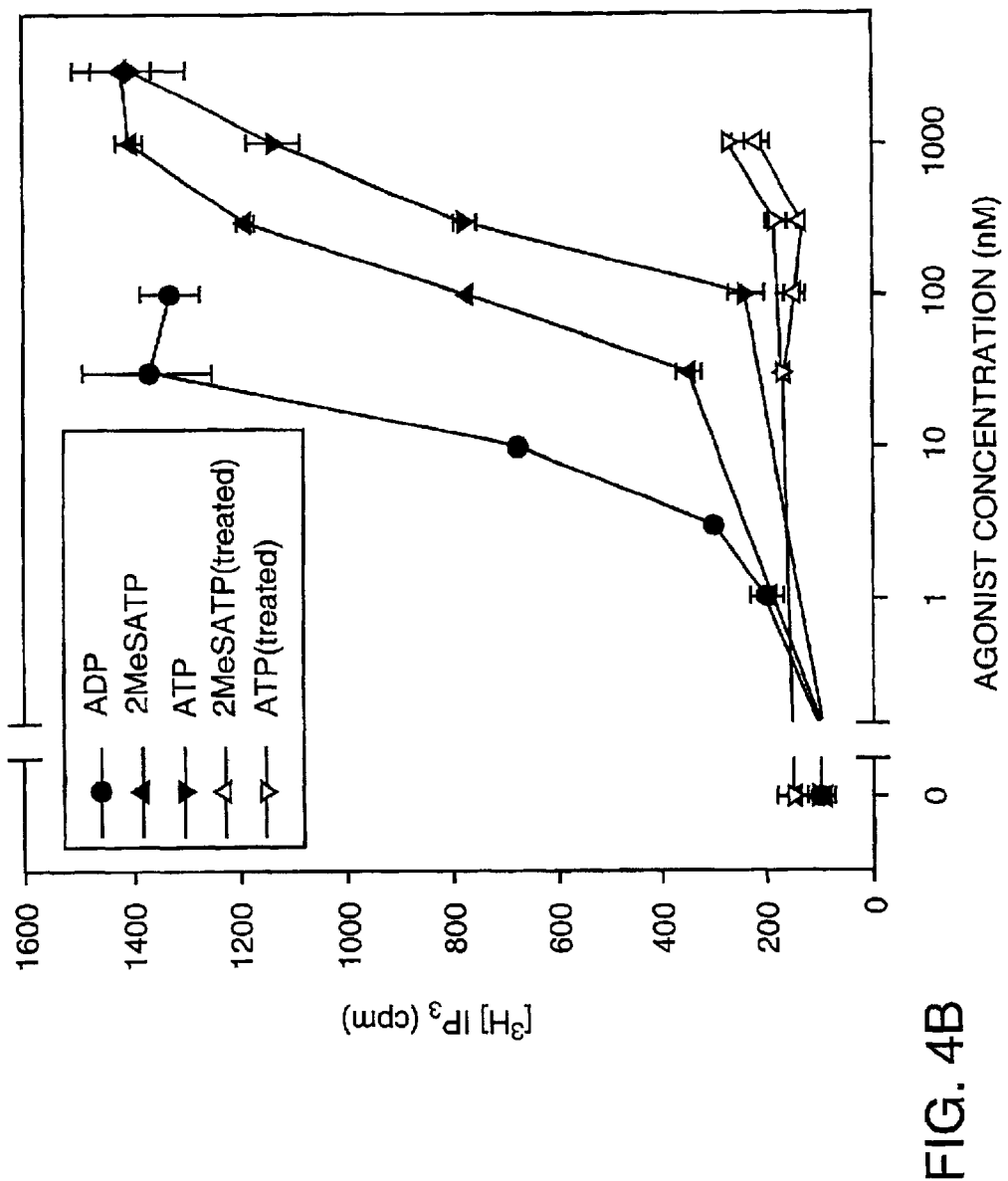

As discussed previously, commercial nucleotide powders are contaminated by degradation products (4, 13, 28). Contamination is usually 1% for ATP and about 10% for 2MeSATP (28). 2MeSATP and ATP solutions (1 mM) were treated at room temperature with 20 units/ml CPK and 10 mM CP during 90 min. This ATP-regenerating system circumvents problems arising from the contamination and degradation of triphosphate nucleotide solutions (28). In these conditions, the responses to ATP and 2MeSATP were abolished (FIG. 4B).

Figure 4C:
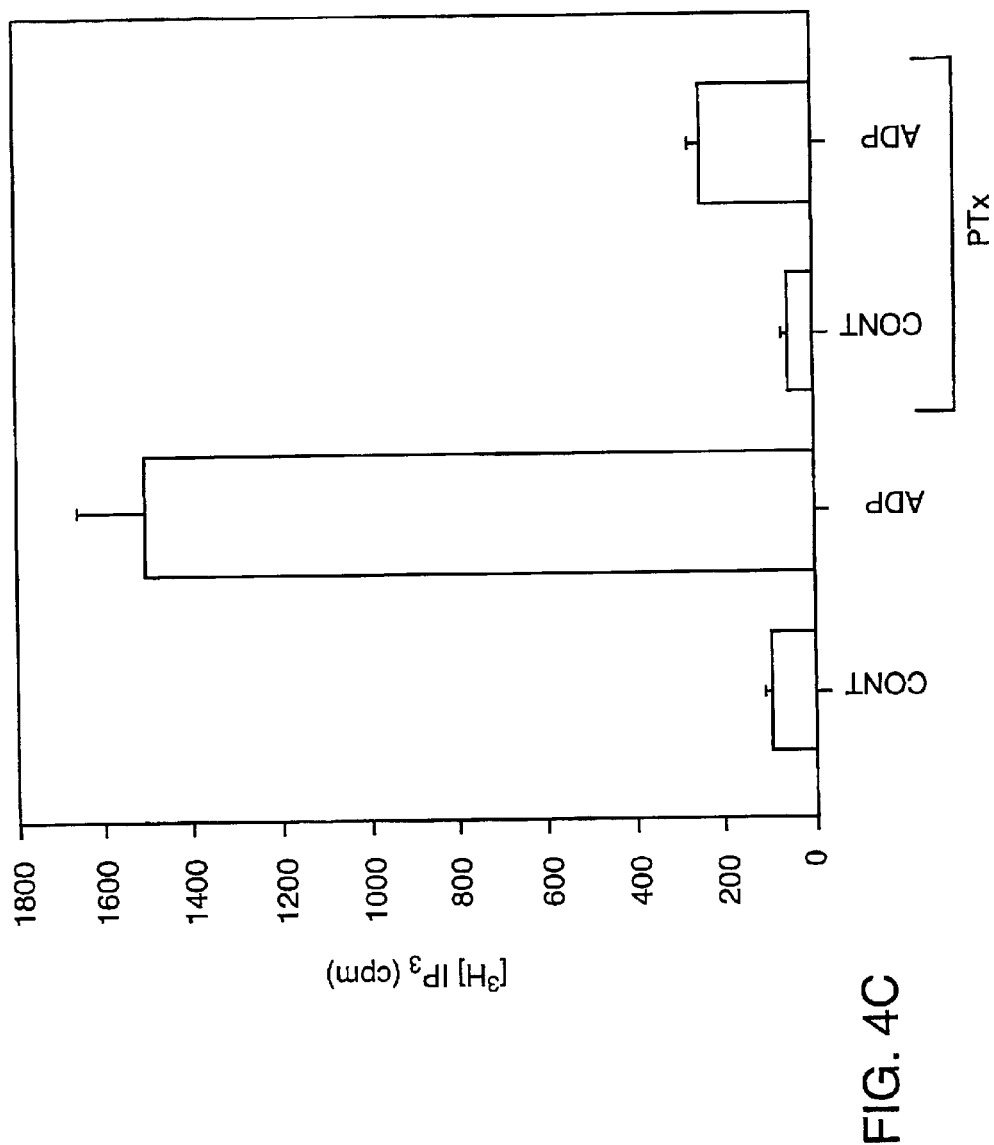

An inhibition of 86±8% (mean±range of two independent experiments) of the ADP response (300 nM) after a 18 hours pretreatment of the transfected cells with 100 ng/ml pertussis toxin (PTx) was observed (FIG. 4C). 1321N1 transfected cells were pre-incubated with or without 100 ng/ml pertussis toxin (PTx) for 18 h and then incubated in the presence of ADP (300 nM) or control medium (CONT) for 30 s. The data represent the mean±S.D. of triplicate experimental points obtained in one representative experiment of two.

Example 4

Stable Expression of the Novel Receptor in CHO-K1 Cells

Figure 5A:
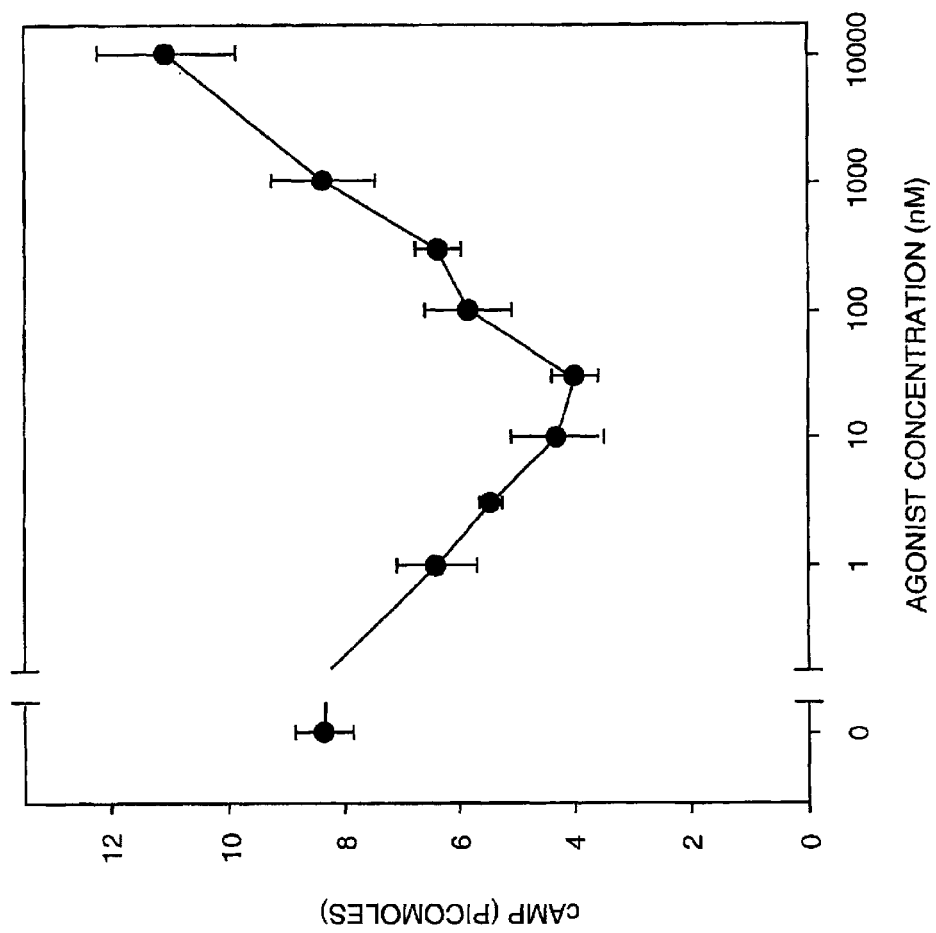
FIGS. 5A and 5B represent respectively a concentration-action curve of ADP on cAMP accumulation in CHO-K1 cells expressing the GPR86 ($P2Y_{13}$) human receptor and the effect of pertussis toxin on cAMP accumulation induced by ADP in CHO-K1 cells expressing the GPR86 ($P2Y_{13}$) human receptor according to the invention.
Figure 5B:
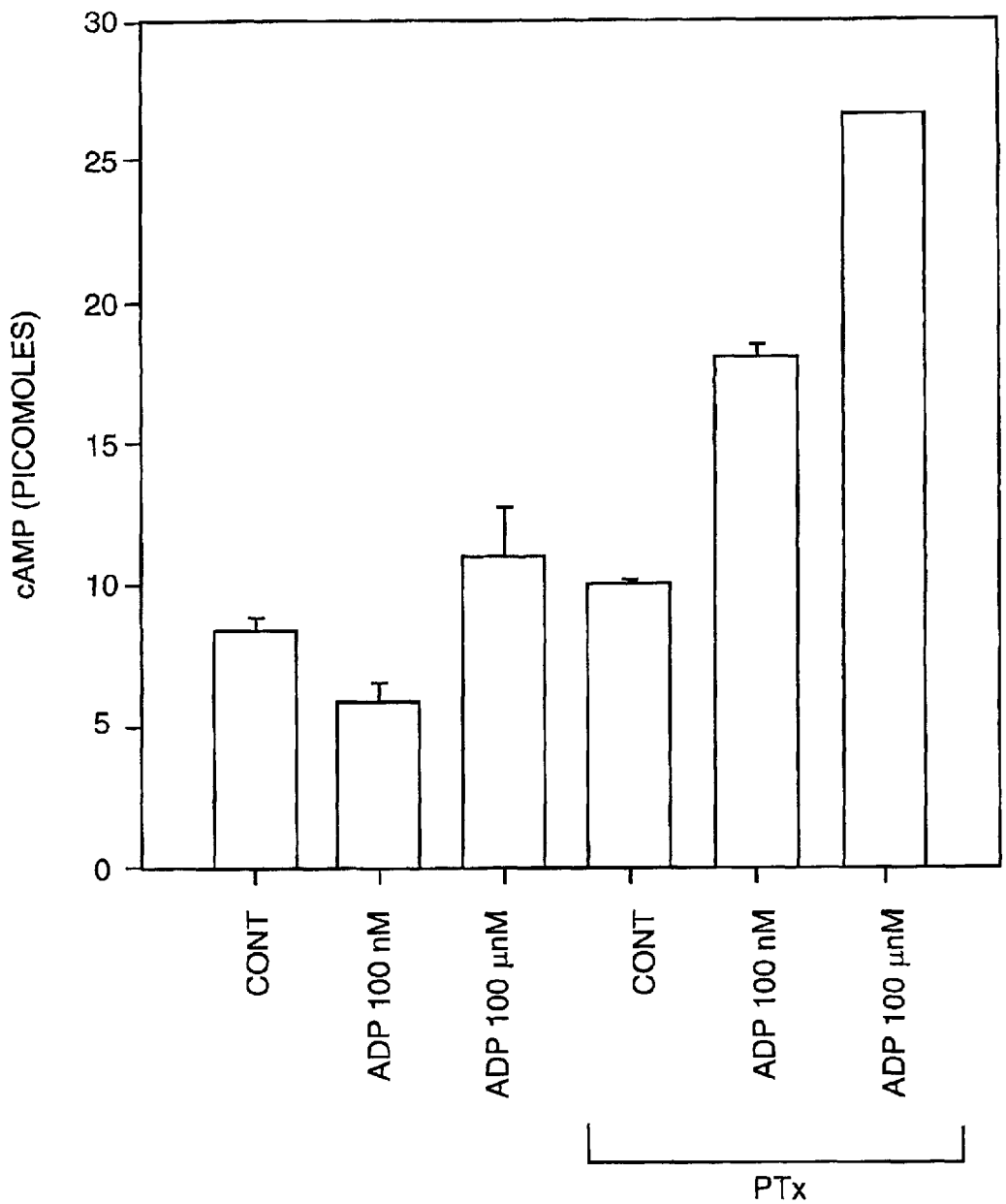

The potential effect of nucleotides was tested on the cAMP pathway in CHO-K1 cells expressing the human GPR86 receptor. Significant inhibitions of the cAMP level were observed at low concentrations of ADP (FIG. 5A) and 2MeSADP in the presence of forskolin (4 μM). CHO-K1 transfected cells were incubated in the presence of various concentrations of ADP and 4 μM forskolin for 10 min. The data represent the mean±S.D. of triplicate experimental points obtained in one representative experiment of three and 2MeSADP in the presence of forskolin 4 $\mu$M. The $IC_{50}$ of ADP was 1.5±0.6 nM (mean±S.D. of three independent experiments) with a maximal inhibition percentage of 52±7% at 30 nM (mean±S.D. of three independent experiments). A second phase was observed at concentrations higher than 30 nM: the inhibition of adenylyl cyclase decreased and a small increase was observed at 10 $\mu$M (FIG. 5A). After an 18 h-pretreatment of the transfected CHO-K1 cells with 100 ng/ml pertussis toxin, ADP (100 nM and 100 $\mu$M) induced significant increases of the cAMP level (FIG. 5B). CHO-K1 transfected cells were incubated in the presence of various concentrations of ADP an 4 $\mu$M forskolin for 10 minutes. The data represent the mean+/−S.D. of triplicate experimental points obtained in one representative experiment of three. CHO-K1 transfected cells were pre-incubated with or without 100 ng/ml pertussis toxin for 18 h and then incubated in the presence of ADP (100 nM and 100 $\mu$M) or water (CONT) and 4 $\mu$M forskolin for 10 min. The data represent the mean±S.D. of triplicate experimental points obtained in one representative experiment of two. The biphasic effect of ADP on adenylyl cyclase has been reproduced in 1321N1 cells transfected with the human GPR86 receptor.

To investigate changes in the activation status of the MAP kinases Erk1 and Erk2 upon stimulation of the human GPR86 receptor, whole CHO-K1 transfected cell extracts were analysed by Western blotting using a specific antibody for the dually phosphorylated kinases (at $Thr^{202}$ and $Tyr^{204}$), which are the active forms of Erk. Western Blot Analysis of phosphorylated Erk1 and Erk2 proteins.

GPR86-transfected CHO-K1 cells were seeded at $1.5 \times 10^6$ cells/dish. After 24 h, the cells were serum-starved for 2 h in KRH buffer. After stimulation with the agonist, the cells were scraped in 1 ml of PBS pH 7.3 (137 mM NaCl, 2.7 mM KCl, 4.3 mM $Na_2HPO_4 \cdot 7H_2O$ and 1.4 mM $KH_2PO_4$). The cells were recovered by centrifugation and lysed in 150 $\mu$l of Laemmli buffer (10% (w/v) glycerol, 5% (v/v) mercaptoethanol, 2.3% (w/v) SDS, 62.5 mM Tris-HCl pH 6.8). The protein concentration was determined using the method of Minamide and Bamburg (27). The same amount of protein for each condition was electrophoresed in a 12% SDS-polyacrylamide gel. Proteins were then transferred overnight at 60 V and 4° C. onto a nitrocellulose membrane using 20 mM Tris, 154 mM glycine, 20% (v/v) methanol as a transfer buffer. Immunodetection was achieved using the enhanced chemiluminescence Western blotting detection system (ECL, Amersham Pharmacia Biotech) using a biotinylated-secondary mouse antibody (1/25,000). The monoclonal antibody specific for the dually phosphorylated forms of Erk1 and Erk2 (at $Thr^{202}$ and $Tyr^{204}$) was used at 1/1000-dilution.

Figure 6A:
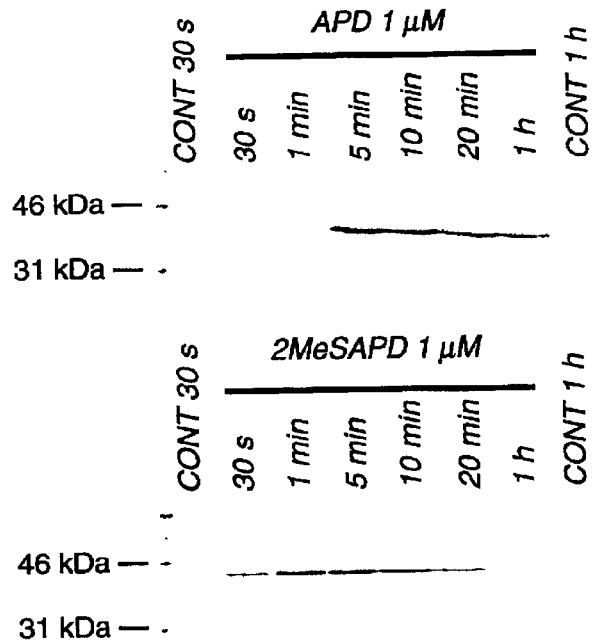
FIGS. 6A and 6B show a western blot analysis of phosphorylated Erk1 and Erk2 proteins in CHO-K1 cells expressing the GPR86 ($P2Y_{13}$) human receptor according to the invention.

In CHO-K1 cells, phosphorylated Erk1 and Erk2 had the predicted molecular mass of 44 and 42 kDa, respectively. Stimulation of the human GPR86 receptor stably expressed in CHO-K1 cells with 1 $\mu$M ADP or 2-MeSADP led to a strong phosphorylation of Erk2 (FIG. 6A). GPR86-transfected CHO-K1 cells were stimulated during different times or with various concentrations of ADP and 2MeSADP or water (CONT). The effect of 100 ng/ml pertussis toxin (PTx) has been tested at 5 and 30 min in the presence of 1 $\mu$M ADP or 2MeSADP. Blotting and immunodetection were achieved as described using the enhanced chemiluminescence Western blotting detection system (ECL, Amersham Pharmacia Biotech).

Figure 6B:
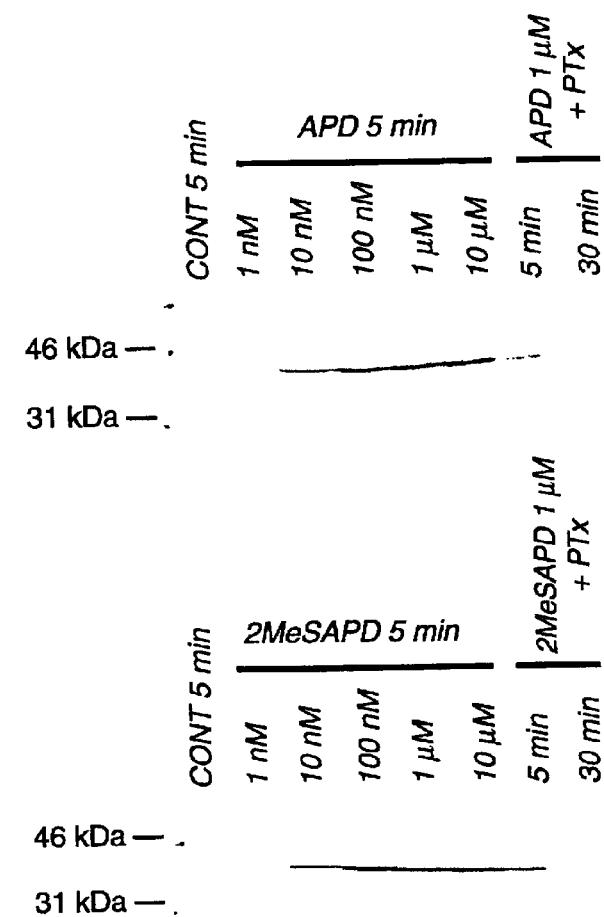
Figure 7:
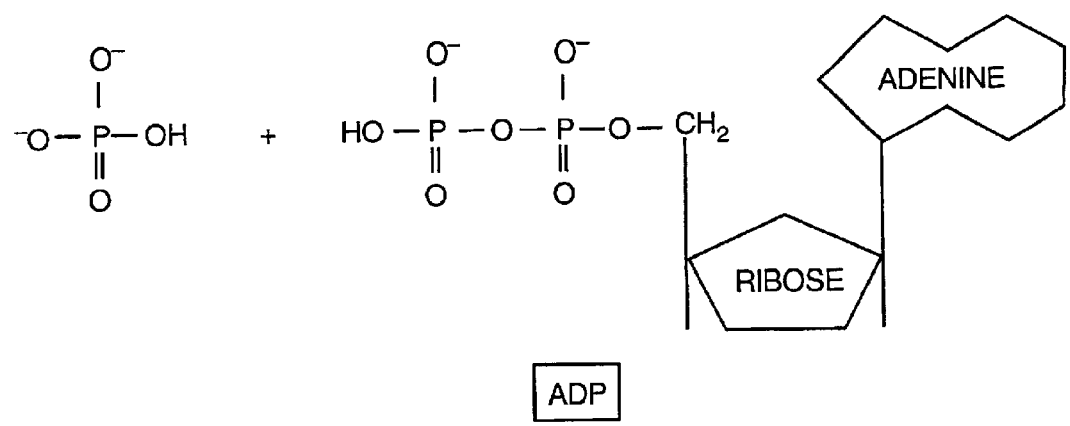
FIG. 7 shows the structure of ADP.

Erk1 was also weakly phosphorylated. Erk phosphorylation was detected after 1 min of stimulation and increased with time (FIG. 6A). The maximal response was obtained after 5 min of stimulation with ADP or with 2-MeSADP, after which Erk activation slowly decreased to the basal level after 1 h. To determine if endogenous receptors can be responsible for ADP or 2-MeSADP-dependent Erk activation in CHO-K1 cells, these nucleotides were tested on cells transfected with the empty pEFIN5 vector: Erk1 or Erk2 phosphorylation were not observed when CHO-K1 control cells were incubated 5 min, 20 min or 1 h with 1 $\mu$M of 2-MeSADP or ADP. The concentration-dependence of the Erk phosphorylation induced by ADP was determined at the peak of the transient response (5 min). Stimulation of the human GPR86 receptor with ADP or 2MeSADP (1 nM to 10 $\mu$M) led to a concentration-dependent phosphorylation of Erk1 and Erk2 (FIG. 6B). A maximal effect was obtained at 1 $\mu$M, but a significant effect was already observed at 10 nM for both agonists. In order to evaluate the involvement of $G_i$ protein in these effects, we pre-incubated GPR86-CHO-K1 transfected cells with pertussis toxin (100 ng/ml for 18 h) prior to the ADP (1 $\mu$M) or the 2-MeSADP (1 $\mu$M) stimulation. The Erk phosphorylation normally induced by 5 or 30 minutes of ADP or 2-MeSADP treatment was strongly inhibited (FIG. 6B).

The cloning and pharmacological characterization of a novel human G-protein-coupled receptor of the P2Y family, tentatively called $P2Y_{13}$ corresponds to the previously described GPR86 orphan receptor (24). Concerning its sequence, the homology with the $P2Y_1$ to $P2Y_{11}$ subtypes is restricted to around 25%. On the contrary, the GPR86 ($P2Y_{13}$) receptor displays a significant homology with the human $P2Y_{12}$ and UDP-glucose receptors. The closest G-coupled receptor is the human $P2Y_{12}$ receptor (48% amino acid identity) which is also a receptor responsive to ADP. Mutagenesis experiments with the $P2Y_2$ receptor have identified three positively charged amino acids in the sixth and seventh transmembrane domains ($His^{262}$, $Arg^{265}$ and $Arg^{292}$), which play a crucial role in nucleotide binding (presumably by neutralizing the negative charge of the phosphate groups) (28). The first two residues are conserved in the GPR86 ($P2Y_{13}$) receptor respectively at positions 251 and 254. These two residues are also conserved in the $P2Y_{12}$ and UDP-glucose receptors. The $Arg^{292}$ residue of the $P2Y_2$ receptor is replaced by a negatively charged glutamate residue in $P2Y_{12}$, GPR86 ($P2Y_{13}$) and UDP-glucose receptors and could have a great importance for the pharmacology of the receptor.

P2Y12 and GPR86 ($P2Y_{13}$) receptors thus form a subgroup of P2Y receptors structurally different from the other P2Y receptors and which share a high affinity for their ligand, ADP. The $EC_{50}$ value of ADP for the GPR86 ($P2Y_{13}$) receptor is 20 to 1000-fold lower than that of the respective ligands of other P2Y receptors in comparable transfected cell lines. From a pharmacological point of view, the relative affinities of ADP and 2MeSADP allow one to discriminate between the $P2Y_{12}$ and GPR86 ($P2Y_{13}$) subtypes. Similar affinities were observed for the GPR86 ($P2Y_{13}$) receptor, whereas 2MeSADP displays a 10 to 100-fold higher potency than ADP for the P2Y12 receptor, depending on the expression system (21, 22).

The presence of the $G\alpha_{16}$ protein was necessary to couple the GPR86 ($P2Y_{13}$) receptor to phospholipase C in 1321N1 cells. The strong inhibitory effect of pertussis toxin on the $IP_3$ accumulation induced by ADP in 1321N1-$G\alpha_{16}$ transfected cells suggests a synergism between $G\alpha_{16}$ and $G_i$ proteins. Such a phenomenon has been described previously in HEL cells, where $Ca^{2+}$ mobilisation by $P2Y_2$ agonists is inhibited completely by $G\alpha_{16}$ antisense and partially by pertussis toxin (29).

Inhibition of adenylyl cyclase and the stimulation of MAP-kinases (ERK-1 and 2) are transduction mechanisms associated to the GPR86 (P2Y,13) receptor and involving both $G_i$ proteins. The biphasic effect of ADP on adenylyl cyclase is reminiscent of what has been observed for other receptors like the $\alpha_2$ adrenergic receptor (30, 31). At low concentrations of agonist, there was an inhibition of adenylyl cyclase whereas an increase was observed at higher concentrations, suggesting the simultaneous coupling to two G-proteins with opposing effects. This simultaneous coupling could be an artefact of surexpression.

Concerning the tissue distribution of the human GPR86 ($P2Y_{13}$) receptor, a good correlation has been obtained between the present RT-PCR data and the Northern blotting data obtained by Wittenberger et al. (24). The human GPR86 ($P2Y_{13}$) receptor is especially expressed in human spleen and brain, where it displays a large expression in different brain regions. The $P2Y_{12}$ receptor is also detected in the human brain and presents a glial expression pattern. Inhibition of cAMP formation by ADP has been described in rat C6 glioma cells (32) and rat brain capillary endothelial cells (33). In both models 2MeSADP was much more potent than ADP and 2MeSATP had a similar potency to 2MeSADP: these features suggest the involvement of $P2Y_{12}$ rather than GPR86 ($P2Y_{13}$) receptors. Expression of the GPR86 ($P2Y_{13}$) receptor in spleen, lymph nodes and bone marrow suggests that it might play a role in hematopoiesis and the immune system.

This invention relates to the use of a human G protein-coupled receptor, GPR86 ($P2Y_{13}$), as a screening tool to identify agonists or antagonists of the aequorin luminescence resulting from expression of this receptor.

The present invention will be described in more details in the following examples in reference to the enclosed figures.

Example 5
Production of a Transgenic Animal

Methods for generating non-human transgenic animals are described herein. DNA constructs can be introduced into the germ line of a mammal to make a transgenic mammal. For example, one or several copies of the construct can be incorporated into the genome of a mammalian embryo by standard transgenic techniques.

In an exemplary embodiment, a transgenic non-human animal is produced by introducing a transgene into the germline of the non-human animal. Transgenes can be introduced into embryonal target cells at various developmental stages. Different methods are used depending on the stage of development of the embryonal target cell. The specific line(s) of any animal used should, if possible, be selected for general good health, good embryo yields, good pronuclear visibility in the embryo, and good reproductive fitness.

Introduction of the $P2Y_{13}$ Receptor protein transgene into the embryo is accomplished by any of a variety of means known in the art such as microinjection, electroporation, or lipofection. For example, an $P2Y_{13}$ Receptor protein transgene is introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg is incubated in vitro for varying amounts of time, or reimplanted into the surrogate host, or both. One common method is to incubate the embryos in vitro for about 1–7 days, depending on the species, and then reimplant them into the surrogate host.

The progeny of the transgenically manipulated embryos are tested for the presence of the construct by Southern blot analysis of a segment of tissue. An embryo having one or more copies of the exogenous cloned construct stably integrated into the genome is used to establish a permanent transgenic mammal line carrying the transgenically introduced construct.

Litters of transgenically altered mammals are assayed after birth for the incorporation of the construct into the genome of the offspring. This is done by hybridizing a probe corresponding to the DNA sequence coding for the fusion protein or a segment thereof onto chromosomal material from the progeny. Those mammalian progeny found to contain at least one copy of the construct in their genome are grown to maturity. The transgenic mammals are bred to produce other transgenic progeny.

Transgenic females are tested for protein expression using an art-known assay technique, e.g. a Western blot or enzymatic assay.

Example 6
GPR86 Activity

The activity of GPR 86 can be detected or measured as follows: Recombinant mammalian cells, for example 1321N1 astrocytoma or CHO-K1 cells, stably transfected with a suitable GPR86 ($P2Y_{13}$) expression vector, are plated out onto tissue culture plates as described in examples 3 and 4. At the appropriate cell density, usually between 50–75% confluency, the culture media is replaced with a KRH buffer solution (Krebs-Ringer Hepes: 124 mM NaCL, 5 mM KCl, 1.25 mM $MgSO_4$, 1.45 mM $CaCl_2$, 1.25 mM $KH_2PO_4$, 25 mM Hepes pH:7.4 and 8 mM glucose) containing ADP ligand (preferably in the range of 1 nM to 1 $\mu$M) and the cells are incubated for an additional 30 s at 37° C. degrees. After this incubation, the cells are washed and lysed. The activity of GPR86 in this cellular extract in the absence or presence of ADP ligand is determined by detecting the associated activity of downstream second messengers such as cAMP, MAP kinase/ERK phosphorylation and IP3 as described in examples 3 and 4. GPR86 activity is defined as a two fold or greater increase in ERK phosphorylation or two fold or greater decrease in cAMP levels in the absence versus the presence of ADP. Activity is also defined by a two fold or preferably greater change in second messenger levels in the presence versus the absence of an optimal concentration of the ligand ADP.

Example 7
Screening for Modulators of GPR86 Activity

Candidate modulators of GPR86 can be identified as follows: The assay described in Example 6 provides a premise for screening different candidate compounds for 'modulating' activity of GPR86. According to this scenario, GPR86 stably transfected cells are co-incubated with an appropriate concentration of ADP ligand (preferably in the range from 1 nM to 1 $\mu$M) and different concentrations of an agonist, inverse agonist, antagonist or other candidate modulator compound (preferably in the range from 0.1 nM to 1 $\mu$M or more). After incubation at room temperature, the cells are washed and lysed. Aliquots of cell extract are then tested in second messenger assays (as described previously in examples 3,4 and 6). In this manner, the effect of modulator compounds on GPR86 activity can be measured by determining the activity of downstream second messengers in the presence or absence of a candidate modulator compound under optimal test conditions of ADP ligand concentration, buffer composition, incubation time and temperature. The assay can also be performed in a high throughput format (as described in the kit section) to simultaneously test multiple candidate modulators at a variety of concentrations. GPR86 activity, in the presence of an optimal concentration of ADP, is determined by detecting any change in second messenger levels in the presence versus the absence of candidate modulator compound at a defined concentration.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

REFERENCES

1. Abbrachio, M. P. and Burnstock, G. (1994) Pharmacol. Ther. 64, 445–475.
2. Fredholm, B. B. et al.(1997) Trends Pharmacol. Sci. 18, 79–82.
3. Webb, T. E. et al. (1993) FEBS Lett. 324, 219–225.
4. Leon, C. et al. (1997) FEBS Lett. 403, 26–30.
5. Communi, D. et al. (1997) J. Biol. Chem. 272, 31969–31973.
6. Lustig, K. D. et al. (1993) Proc. Natl. Acad. Sci. U.S.A. 90, 5113–5117.
7. Parr, C. E. et al. (1994) Proc. Natl. Acad. Sci. U.S.A. 91, 3275–3279.
8. Bogdanov, Y. et al. (1997) J. Biol. Chem. 272, 12583–12590.
9. Boyer, J. L. et al. (2000) Mol. Pharmacol. 57, 805–810.
10. Webb, T. E. et al. (1996) Mol. Pharmacol. 50, 258–265.
11. Chang, K. et al. (1995) J. Biol. Chem. 270, 26152–26158.
12. Communi, D. et al. (1996) Biochem. Biophys. Res. Commun. 222, 303–308.
13. Nicholas, R. A. et al. (1996) Mol. Pharmacol. 50, 224–229.
14. Communi, D. et al. (1995) J. Biol. Chem. 270, 30849–30852.
15. Nguyen, T. et al. (1995) J. Biol. Chem. 270, 30845–30848.
16. Webb, T. E. et al. (1996) Biochem. Biophys. Res. Commun. 219, 105–110.
17. Akbar, G. K. M. et al. (1996) J. Biol. Chem. 271, 18363–18367.
18. Yokomizo, T. et al. (1997) Nature 387, 620–624.
19. Li, Q. et al. (1997) Biochem. Biophys. Res. Commun. 236, 455–460.
20. Janssens, R. et al. (1997) Biochem. Biophys. Res. Commun. 226, 106–112.
21. Zhang, F. L et al. (2001) J. Biol. Chem. 276 (11), 8608–8615.
22. Hollopeter, G. et al. (2001) Nature 409, 202–207.
23. CHAMBERS, J. K. ET AL. (2000) J. BIOL. CHEM. 275 (15), 10767–10771.
24. Wittenberger, T. et al. (2001) J. Mol. Biol. 307, 799–813.
25. Communi, D. et al. (1995b). Circ. Res., 76, 191–198.
26. Brooker, G. et al. (1979) Adv. Cyclic Nucleotide Res. 10, 1–33.
27. Minamide, L. S. and Bamburg, J. R. (1990) Anal. Biochem. 190, 66–70.
28. Erb, L. et al. (1995) J. Biol. Chem. 270,4185–4188.
29. Baltensperger, K. and Porzig, H. (1997) J. Biol. Chem. 272, 10151–10159.
30. Eason, M. G. et al. (1992) J. Biol. Chem. 267 (22), 15795–15801.
31. Chabre, O. et al. (1994) J. Biol. Chem. 269 (8), 5730–5734.
32. Boyer, J. L. et al. (1993) J. Pharmacol. Exp. Ther. 267, 1140–1146.
33. Simon, J. et al. (2001) Br. J. Pharmacol. 132, 173–182.
34. Gudermann et al. (1995) J. Mol. Med. 73, 51–63.

What is claimed is:

1. A method of identifying an agent that binds to GPR86, said method comprising:
   (a) contacting a GPR86 polypeptide having the sequence of SEQ ID NO:2 with a compound selected from the group consisting of ADP, 2MeSADP and ADPbetaS in the presence or absence of a candidate binding agent under conditions permitting binding of said compound to said GPR86 polypeptide; and
   (b) measuring binding of said compound to said GPR86 polypeptide, wherein a decrease in binding in the presence of said candidate binding agent, relative to binding in absence of said candidate binding agent, identifies said candidate binding agent as an agent that binds to GPR86.

2. A method of detecting in a sample the presence of an agent that binds to GPR86, said method comprising:
   (a) contacting a GPR86 polypeptide having the sequence of SEQ ID NO:2 with a compound selected from the group consisting of ADP, 2MeSADP and ADPbetaS in the presence or absence of said sample under conditions permitting binding of said compound to said GPR86 polypeptide; and
   (b) measuring binding of said compound to said GPR86 polypeptide, wherein a decrease in binding in the presence of said sample, relative to binding in the absence of said sample, indicates the presence; in said sample of an agent that binds to GPR86.

3. A method of identifying an agonist that increase the signaling of GPR86 having the sequence of SEQ ID NO:2, said method comprising:
   (a) contacting a GPR86 polypeptide with a candidate modulator;
   (b) measuring a signaling activity of said GPR86 polypeptide in the presence of said candidate modulator; and
   (c) comparing said activity measured in the presence of said candidate modulator to said activity measured in a reaction in which said GPR86 polypeptide is contacted with a compound selected from the group consisting of ADP, 2MeSADP and ADPbetaS, wherein said candidate modulator is identified as an agonist that increases the signaling of GPR86 when the amount of said activity measured in the presence of said candidate modulator is at least 10% of the amount induced by said compound.

4. A method of detecting in a sample the presence of an agent that increases the signaling of GPR86 having the sequence of SEQ ID NO:2, said method comprising:
   (a) contacting a GPR86 polypeptide with said sample;
   (b) measuring a signaling activity of said GPR86 polypeptide in the presence of said sample; and
   (c) comparing said activity measured in the presence of said sample to said activity measured in a reaction in which said GPR86 polypeptide is contacted with a compound selected from the group consisting of ADP, 2MeSADP and ADPbetaS, wherein an agonist that increases the signaling of GPR86 is detected if the amount of said activity measured in the presence of said sample is at least 10% of the amount induced by said compound.

5. A method of identifying an agent that decreases the signaling activity of GPR86 having the sequence of SEQ ID NO:2, said method comprising:
   (a) contacting a GPR86 polypeptide with a compound selected from the group consisting of ADP, 2MeSADP and ADPbetaS in the presence or absence of said agent;
   (b) measuring a signaling activity of said GPR86 polypeptide; and
   (c) comparing the amount of said activity measured in a reaction containing GPR86 and said compound without said agent to the amount of said activity measured in a reaction containing GPR86, said compound and said agent, wherein a decrease in said activity in the presence of said agent relative to the activity in the absence of said agent indicates that this agent is an antagonist for GPR86.

6. A method of detecting in a sample the presence of an agent that decreases the signaling activity of GPR86 having the sequence of SEQ ID NO:2, said method comprising:
   (a) contacting a GPR86 polypeptide with a compound selected from the group consisting of ADP, 2MeSADP and ADPbetaS in the presence or absence of said sample;
   (b) measuring a signaling activity of said GPR86 polypeptide; and
   (c) comparing the amount of said activity measured in a reaction containing GPR86 and said compound without said sample to the amount of said activity measured in a reaction containing GPR86, said compound and said sample, wherein a decrease in said activity in the presence of said sample relative to the activity in the absence of said sample indicates the presence, in said sample, of an antagonist for GPR86.

7. The method according to any of claims 1 to 6 wherein said GPR86 having the sequence of SEQ ID NO:2 is expressed by cells.

8. The method according to any of claims 1 to 6 wherein said GPR86 having the sequence of SEQ ID NO:2 is present in cell membranes.

9. The method according to any of claims 1 to 6, wherein said GPR86 having the sequence of SEQ ID NO:2 is present in or on virus-induced budding membranes.

10. The method according to claims 7 or 8 wherein said cells are selected from the group consisting of: COS7-cells, a CHO cell, a LM (TK−) cell, a NIH-3T3 cell, HEK-293 cell, K-562 cell and an 1321N1 astrocytoma cell.

11. The method according to any of claims 1 to 6, further performed in the presence of Gα16 polypeptide.

12. The method according to any of claims 1 to 6 wherein said measuring or said detecting is performed using a method selected from label displacement, surface plasmon resonance, fluorescence resonance energy transfer, fluorescence quenching, and fluorescence polarization.

13. The method according to any of claims 1 to 6 wherein said detecting or measuring a signaling activity or measuring the binding of said GPR86 polypeptide comprises detecting a change in the level of a second messenger.

14. The method according to any of claims 1 to 6 wherein the step of detecting a signaling activity or said measuring a signaling activity or measuring the binding comprises measurement of guanine nucleotide binding or exchange, adenylate cyclase activity, cAMP, protein kinase C activity, phosphatidylinositol breakdown, diacylglycerol, inositol triphosphate, intracellular calcium, arachinoid acid concentration, MAP kinase activity, tyrosine kinase activity or reporter gene expression.

15. The method of claim 14 wherein said measuring a signaling activity comprises using an aequorin-based assay.

* * * * *

SEQUENCE LISTING

<160> NUMBER OF SEQ ID NOS: 9

<210> SEQ ID NO 1
<211> LENGTH: 1002
<212> TYPE: DNA
<213> ORGANISM: Homo sapiens

<400> SEQUENCE: 1

```
atgaacacca cagtgatgca aggcttcaac agatctgagc ggtgcccag agacactcgg      60 atagtacagc tggtattccc agccctctac acagtggttt tcttgaccgg catcctgctg     120
aatactttgg ctctgtgggt gtttgttcac atccccagct cctccacctt catcatctac     180
ctcaaaaaca ctttggtggc cgacttgata atgacactca tgcttccttt caaaatcctc     240
tctgactcac acctggcacc ctggcagctc agagcttttg tgtgtcgttt ttcttcggtg     300
atattttatg agaccatgta tgtgggcatc gtgctgttag ggctcatagc ctttgacaga     360
ttcctcaaga tcatcagacc tttgagaaat attttttctaa aaaaacctgt ttttgcaaaa     420
acggtctcaa tcttcatctg gttcttttttg ttcttcatct ccctgccaaa tatgatcttg     480
agcaacaagg aagcaacacc atcgtctgtg aaaaagtgtg cttccttaaa ggggcctctg     540
gggctgaaat ggcatcaaat ggtaaataac atatgccagt ttattttctg gactgttttt     600
atcctaatgc ttgtgttta tgtggttatt gcaaaaaaag tatatgattc ttatagaaag     660
```

```
tccaaaagta aggacagaaa aaacaacaaa aagctggaag gcaaagtatt tgttgtcgtg    720
gctgtcttct ttgtgtgttt tgctccattt catttttgcca gagttccata tactcacagt    780
caaaccaaca ataagactga ctgtagactg caaaatcaac tgtttattgc taaagaaaca    840
actctctttt tggcagcaac taacattgt atggatccct aatatacat attcttatgt    900 aaaaaattca cagaaaagct accatgtatg caagggagaa agaccacagc atcaagccaa    960
gaaaatcata gcagtcagac agacaacata accttaggct ga                      1002
```

<210> SEQ ID NO 2
<211> LENGTH: 333
<212> TYPE: PRT
<213> ORGANISM: Homo sapiens

<400> SEQUENCE: 2

```
Met Asn Thr Thr Val Met Gln Gly Phe Asn Arg Ser Glu Arg Cys Pro
1               5                   10                  15

Arg Asp Thr Arg Ile Val Gln Leu Val Phe Pro Ala Leu Tyr Thr Val
            20                  25                  30

Val Phe Leu Thr Gly Ile Leu Leu Asn Thr Leu Ala Leu Trp Val Phe
        35                  40                  45

Val His Ile Pro Ser Ser Thr Phe Ile Ile Tyr Leu Lys Asn Thr
    50                  55                  60

Leu Val Ala Asp Leu Ile Met Thr Leu Met Leu Pro Phe Lys Ile Leu
65                  70                  75                  80

Ser Asp Ser His Leu Ala Pro Trp Gln Leu Arg Ala Phe Val Cys Arg
                85                  90                  95

Phe Ser Ser Val Ile Phe Tyr Glu Thr Met Tyr Val Gly Ile Val Leu
            100                 105                 110

Leu Gly Leu Ile Ala Phe Asp Arg Phe Leu Lys Ile Ile Arg Pro Leu
        115                 120                 125

Arg Asn Ile Phe Leu Lys Lys Pro Val Phe Ala Lys Thr Val Ser Ile
    130                 135                 140

Phe Ile Trp Phe Phe Leu Phe Phe Ile Ser Leu Pro Asn Met Ile Leu
145                 150                 155                 160

Ser Asn Lys Glu Ala Thr Pro Ser Ser Val Lys Lys Cys Ala Ser Leu
                165                 170                 175

Lys Gly Pro Leu Gly Leu Lys Trp His Gln Met Val Asn Asn Ile Cys
            180                 185                 190

Gln Phe Ile Phe Trp Thr Val Phe Ile Leu Met Leu Val Phe Tyr Val
        195                 200                 205

Val Ile Ala Lys Lys Val Tyr Asp Ser Tyr Arg Lys Ser Lys Ser Lys
    210                 215                 220

Asp Arg Lys Asn Asn Lys Lys Leu Glu Gly Lys Val Phe Val Val Val
225                 230                 235                 240

Ala Val Phe Phe Val Cys Phe Ala Pro Phe His Phe Ala Arg Val Pro
                245                 250                 255

Tyr Thr His Ser Gln Thr Asn Asn Lys Thr Asp Cys Arg Leu Gln Asn
            260                 265                 270

Gln Leu Phe Ile Ala Lys Glu Thr Thr Leu Phe Leu Ala Ala Thr Asn
        275                 280                 285

Ile Cys Met Asp Pro Leu Ile Tyr Ile Phe Leu Cys Lys Lys Phe Thr
    290                 295                 300

Glu Lys Leu Pro Cys Met Gln Gly Arg Lys Thr Thr Ala Ser Ser Gln
305                 310                 315                 320
```

Glu Asn His Ser Ser Gln Thr Asp Asn Ile Thr Leu Gly
              325                 330

<210> SEQ ID NO 3
<211> LENGTH: 11
<212> TYPE: DNA
<213> ORGANISM: Artificial Sequence
<220> FEATURE:
<221> NAME/KEY: misc_binding
<222> LOCATION: (1)..(11)
<223> OTHER INFORMATION: NF-kB binding element

<400> SEQUENCE: 3
ggggactttc c                                                          11

<210> SEQ ID NO 4
<211> LENGTH: 31
<212> TYPE: DNA
<213> ORGANISM: Artificial Sequence
<220> FEATURE:
<221> NAME/KEY: primer
<222> LOCATION: (1)..(31)
<223> OTHER INFORMATION: GPR86 human receptor: a sense primer

<400> SEQUENCE: 4
ccggaattca ccatgaacac cacagtgatg c                                    31

<210> SEQ ID NO 5
<211> LENGTH: 31
<212> TYPE: DNA
<213> ORGANISM: Artificial Sequence
<220> FEATURE:
<221> NAME/KEY: primer
<222> LOCATION: (1)..(31)
<223> OTHER INFORMATION: GPR86 human receptor: anti-sense primer

<400> SEQUENCE: 5
cttgtctaga tcagcctaag gttatgttgt c                                    31

<210> SEQ ID NO 6
<211> LENGTH: 20
<212> TYPE: DNA
<213> ORGANISM: Artificial Sequence
<220> FEATURE:
<221> NAME/KEY: primer
<222> LOCATION: (1)..(20)
<223> OTHER INFORMATION: GPR86 sense primer

<400> SEQUENCE: 6
tgtgtcgttt ttcttcggtg                                                 20

<210> SEQ ID NO 7
<211> LENGTH: 18
<212> TYPE: DNA
<213> ORGANISM: Artificial Sequence
<220> FEATURE:
<221> NAME/KEY: primer
<222> LOCATION: (1)..(18)
<223> OTHER INFORMATION: GPR86 antisense primer

<400> SEQUENCE: 7
ctgccaaaaa gagagttg                                                   18

<210> SEQ ID NO 8
<211> LENGTH: 20
<212> TYPE: DNA
<213> ORGANISM: Artificial Sequence -continued

```
<220> FEATURE:
<221> NAME/KEY: primer
<222> LOCATION: (1)..(20)
<223> OTHER INFORMATION: aldolase sense primer

<400> SEQUENCE: 8
ggcaagggca tcctggctgc                                           20

<210> SEQ ID NO 9
<211> LENGTH: 23
<212> TYPE: DNA
<213> ORGANISM: Artificial Sequence
<220> FEATURE:
<221> NAME/KEY: primer
<222> LOCATION: (1)..(23)
<223> OTHER INFORMATION: aldolase antisense reverse primer

<400> SEQUENCE: 9
taacgggcca gaacattggc att                                       23
```